United States Patent
Sinko et al.

(10) Patent No.: US 9,421,272 B2
(45) Date of Patent: Aug. 23, 2016

(54) NANOCARRIER COMPOSITIONS AND METHODS

(75) Inventors: Patrick J. Sinko, Annandale, NJ (US); Stanley Stein, East Brunswick, NJ (US); Simi Gunaseelan, North Brunswick, NJ (US); Shahriar Pooyan, Mount Kisco, NY (US); Matthew Sean Palombo, Marmora, NJ (US); Xiaoping Zhang, Piscataway, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 13/255,635

(22) PCT Filed: Mar. 16, 2010

(86) PCT No.: PCT/US2010/027532
§ 371 (c)(1),
(2), (4) Date: Dec. 15, 2011

(87) PCT Pub. No.: WO2010/107831
PCT Pub. Date: Sep. 23, 2010

(65) Prior Publication Data
US 2012/0093723 A1    Apr. 19, 2012

Related U.S. Application Data

(60) Provisional application No. 61/160,575, filed on Mar. 16, 2009.

(51) Int. Cl.
| | | |
|---|---|---|
| A61K 51/00 | (2006.01) |
| A61K 39/00 | (2006.01) |
| C12N 9/96 | (2006.01) |
| A61K 38/00 | (2006.01) |
| C07K 16/00 | (2006.01) |
| A61K 49/00 | (2006.01) |
| A61K 38/54 | (2006.01) |
| A61K 47/42 | (2006.01) |
| A61K 9/51 | (2006.01) |
| B82Y 5/00 | (2011.01) |

(52) U.S. Cl.
CPC .............. *A61K 47/42* (2013.01); *A61K 9/5169* (2013.01)

(58) Field of Classification Search
None
See application file for complete search history.

(56) References Cited

U.S. PATENT DOCUMENTS

2008/0188399 A1    8/2008  Sinko et al.
2009/0074828 A1 *  3/2009  Alexis et al. .................. 424/422

FOREIGN PATENT DOCUMENTS

WO    WO 2006/089156 A2 *  8/2006  ......................... 514/2
WO    WO 2006089156 A2 *   8/2006

OTHER PUBLICATIONS

Wan, et al. "Optimizing size and copy number for PEG-fMLF(N-formyl-methionyl-leucyl-phenyalanine) nanocarrier uptake by macrophages." Bioconj. Chem. 19(1): 28-38. Jan. 2008.
Gunaseelan et al. "Multimeric peptide-based PEG nanocarriers with programmable elimination properties." Biomaterials 30: 5649-5659. Jul. 2009.

* cited by examiner

*Primary Examiner* — Amber D Steele
*Assistant Examiner* — Schuyler Milton
(74) *Attorney, Agent, or Firm* — Fox Rothschild LLP

(57) ABSTRACT

This invention provides multimeric nanocarrier for in vivo delivery of a bioactive agent, comprising at least two peptide monomers reversibly or irreversibly linked with one or more of said bioactive agents, wherein said two or more of said peptide monomers are covalently linked by a biodegradable difunctional moiety, as well as methods of using this nanocarrier.

19 Claims, 17 Drawing Sheets

(a) $CH_3CO\text{-}(Lys\text{-}\beta Ala\text{-}\beta Ala)_x\text{-}Cys\text{-}CONH_2$ (b) $CH_3CO\text{-}(Lys\text{-}\beta Ala\text{-}\beta Ala)_x\text{-}(Cys\text{-}\beta Ala\text{-}\beta Ala)_y\text{-}CONH_2$ R = H (free side chain) 0-3 copies
Texas Red 1-4 copies

[a] (i) 3 equiv of fluorescein-PEG5kDa-NHS in (a) 30% DMSO in 100 mM PB pH 7.4 (b) 70% DMSO in 100 mM PB pH 7.4
(ii) 20 equiv of DTT in 100 mM PB pH 8.0
(iii) mixing 2-arm TP-protected Cys with 2-arm free Cys in 100 mM PB pH 7.4
[b] = fluorescein

SEQUENCE LISTING

```
<160> NUMBER OF SEQ ID NOS: 21

<210> SEQ ID NO 1
<211> LENGTH: 6
<212> TYPE: PRT
<213> ORGANISM: Artificial
<220> FEATURE:
<223> OTHER INFORMATION: peptide backbone monomer
<220> FEATURE:
<221> NAME/KEY: bAla
<222> LOCATION: (2)..(3)
<220> FEATURE:
<221> NAME/KEY: bAla
<222> LOCATION: (5)..(5)

<400> SEQUENCE: 1

Lys Ala Ala Lys Ala Cys
1               5

<210> SEQ ID NO 2
<211> LENGTH: 7
<212> TYPE: PRT
```

```
<213> ORGANISM: Artificial
<220> FEATURE:
<223> OTHER INFORMATION: peptide backbone monomer
<220> FEATURE:
<221> NAME/KEY: bAla
<222> LOCATION: (2)..(3)
<220> FEATURE:
<221> NAME/KEY: bAla
<222> LOCATION: (5)..(5)
<220> FEATURE:
<221> NAME/KEY: bAla
<222> LOCATION: (7)..(7)

<400> SEQUENCE: 2

Lys Ala Ala Lys Ala Cys Ala
1               5

<210> SEQ ID NO 3
<211> LENGTH: 10
<212> TYPE: PRT
<213> ORGANISM: Artificial
<220> FEATURE:
<223> OTHER INFORMATION: peptide backbone monomer
<220> FEATURE:
<221> NAME/KEY: bAla
<222> LOCATION: (2)..(3)
<220> FEATURE:
<221> NAME/KEY: bAla
<222> LOCATION: (5)..(6)
<220> FEATURE:
<221> NAME/KEY: bAla
<222> LOCATION: (8)..(9)

<400> SEQUENCE: 3

Cys Ala Ala Lys Ala Ala Lys Ala Ala Lys
1               5                   10

<210> SEQ ID NO 4
<211> LENGTH: 9
<212> TYPE: PRT
<213> ORGANISM: Artificial
<220> FEATURE:
<223> OTHER INFORMATION: peptide backbone monomer
<220> FEATURE:
<221> NAME/KEY: bAla
<222> LOCATION: (1)..(2)
<220> FEATURE:
<221> NAME/KEY: bAla
<222> LOCATION: (4)..(5)
<220> FEATURE:
<221> NAME/KEY: bAla
<222> LOCATION: (7)..(8)

<400> SEQUENCE: 4

Ala Ala Cys Ala Ala Lys Ala Ala Lys
1               5

<210> SEQ ID NO 5
<211> LENGTH: 7
<212> TYPE: PRT
<213> ORGANISM: Artificial
<220> FEATURE:
<223> OTHER INFORMATION: peptide backbone monomer
<220> FEATURE:
<221> NAME/KEY: bAla
<222> LOCATION: (2)..(3)
<220> FEATURE:
<221> NAME/KEY: bAla
<222> LOCATION: (5)..(6)

<400> SEQUENCE: 5

Cys Ala Ala Lys Ala Ala Lys
```

-continued

```
<210> SEQ ID NO 6
<211> LENGTH: 7
<212> TYPE: PRT
<213> ORGANISM: Artificial
<220> FEATURE:
<223> OTHER INFORMATION: peptide backbone monomer
<220> FEATURE:
<221> NAME/KEY: bAla
<222> LOCATION: (2)..(3)
<220> FEATURE:
<221> NAME/KEY: bAla
<222> LOCATION: (5)..(6)

<400> SEQUENCE: 6

Lys Ala Ala Lys Ala Ala Cys
1               5

<210> SEQ ID NO 7
<211> LENGTH: 13
<212> TYPE: PRT
<213> ORGANISM: Artificial
<220> FEATURE:
<223> OTHER INFORMATION: peptide backbone monomer
<220> FEATURE:
<221> NAME/KEY: bAla
<222> LOCATION: (2)..(3)
<220> FEATURE:
<221> NAME/KEY: bAla
<222> LOCATION: (5)..(6)
<220> FEATURE:
<221> NAME/KEY: bAla
<222> LOCATION: (8)..(9)
<220> FEATURE:
<221> NAME/KEY: bAla
<222> LOCATION: (11)..(12)

<400> SEQUENCE: 7

Lys Ala Ala Lys Ala Ala Lys Ala Ala Lys Ala Ala Cys
1               5                   10

<210> SEQ ID NO 8
<211> LENGTH: 13
<212> TYPE: PRT
<213> ORGANISM: Artificial
<220> FEATURE:
<223> OTHER INFORMATION: peptide backbone monomer
<220> FEATURE:
<221> NAME/KEY: bAla
<222> LOCATION: (2)..(2)
<220> FEATURE:
<221> NAME/KEY: bAla
<222> LOCATION: (4)..(4)
<220> FEATURE:
<221> NAME/KEY: bAla
<222> LOCATION: (6)..(6)
<220> FEATURE:
<221> NAME/KEY: bAla
<222> LOCATION: (8)..(8)
<220> FEATURE:
<221> NAME/KEY: bAla
<222> LOCATION: (10)..(10)
<220> FEATURE:
<221> NAME/KEY: bAla
<222> LOCATION: (12)..(12)

<400> SEQUENCE: 8

Cys Ala Lys Ala Lys Ala Lys Ala Lys Ala Lys Ala Cys
1               5                   10

<210> SEQ ID NO 9
```

```
<211> LENGTH: 5
<212> TYPE: PRT
<213> ORGANISM: Artificial
<220> FEATURE:
<223> OTHER INFORMATION: peptide linker

<400> SEQUENCE: 9

Glu Leu Gly Leu Gly
1               5

<210> SEQ ID NO 10
<211> LENGTH: 4
<212> TYPE: PRT
<213> ORGANISM: Artificial
<220> FEATURE:
<223> OTHER INFORMATION: peptide linker

<400> SEQUENCE: 10

Arg Gly Asp Cys
1

<210> SEQ ID NO 11
<211> LENGTH: 5
<212> TYPE: PRT
<213> ORGANISM: Artificial
<220> FEATURE:
<223> OTHER INFORMATION: peptide linker

<400> SEQUENCE: 11

Gly Arg Gly Asp Ser
1               5

<210> SEQ ID NO 12
<211> LENGTH: 6
<212> TYPE: PRT
<213> ORGANISM: Artificial
<220> FEATURE:
<223> OTHER INFORMATION: peptide linker

<400> SEQUENCE: 12

Gly Arg Gly Asp Ser Pro
1               5

<210> SEQ ID NO 13
<211> LENGTH: 5
<212> TYPE: PRT
<213> ORGANISM: Artificial
<220> FEATURE:
<223> OTHER INFORMATION: peptide linker

<400> SEQUENCE: 13

Arg Gly Asp Tyr Lys
1               5

<210> SEQ ID NO 14
<211> LENGTH: 11
<212> TYPE: PRT
<213> ORGANISM: Artificial
<220> FEATURE:
<223> OTHER INFORMATION: cell uptake promoter peptide
<220> FEATURE:
<221> NAME/KEY: misc_feature
<222> LOCATION: (10)..(10)
<223> OTHER INFORMATION: Xaa is Cyc or Lys
<220> FEATURE:
<221> NAME/KEY: misc_feature
<222> LOCATION: (10)..(10)
<223> OTHER INFORMATION: Xaa is modified with biotin
```

```
<400> SEQUENCE: 14

Arg Lys Lys Arg Arg Gln Arg Arg Xaa Cys
1               5                   10

<210> SEQ ID NO 15
<211> LENGTH: 7
<212> TYPE: PRT
<213> ORGANISM: Artificial
<220> FEATURE:
<223> OTHER INFORMATION: organ-specific targeting moieties

<400> SEQUENCE: 15

Cys Leu Pro Val Ala Ser Cys
1               5

<210> SEQ ID NO 16
<211> LENGTH: 7
<212> TYPE: PRT
<213> ORGANISM: Artificial
<220> FEATURE:
<223> OTHER INFORMATION: organ-specific targeting moieties

<400> SEQUENCE: 16

Cys Gly Ala Arg Glu Met Cys
1               5

<210> SEQ ID NO 17
<211> LENGTH: 9
<212> TYPE: PRT
<213> ORGANISM: Artificial
<220> FEATURE:
<223> OTHER INFORMATION: organ-specific targeting moieties

<400> SEQUENCE: 17

Cys Asn Ser Arg Leu His Leu Arg Cys
1               5

<210> SEQ ID NO 18
<211> LENGTH: 9
<212> TYPE: PRT
<213> ORGANISM: Artificial
<220> FEATURE:
<223> OTHER INFORMATION: organ-specific targeting moieties

<400> SEQUENCE: 18

Cys Glu Asn Trp Trp Gly Asp Val Cys
1               5

<210> SEQ ID NO 19
<211> LENGTH: 21
<212> TYPE: PRT
<213> ORGANISM: Artificial
<220> FEATURE:
<223> OTHER INFORMATION: organ-specific targeting moieties

<400> SEQUENCE: 19

Trp Arg Cys Val Leu Arg Glu Gly Pro Ala Gly Gly Cys Ala Trp Phe
1               5                   10                  15

Asn Arg His Arg Leu
            20

<210> SEQ ID NO 20
<211> LENGTH: 4
<212> TYPE: PRT
<213> ORGANISM: Artificial
<220> FEATURE:
```

```
<223> OTHER INFORMATION: peptide monomer backbone
<220> FEATURE:
<221> NAME/KEY: misc_feature
<222> LOCATION: (1)..(1)
<223> OTHER INFORMATION: Lys may optionally be modified with biotin
<220> FEATURE:
<221> NAME/KEY: misc_feature
<222> LOCATION: (2)..(4)
<223> OTHER INFORMATION: Cys may optionally be modified with PEG

<400> SEQUENCE: 20

Lys Cys Cys Cys
1

<210> SEQ ID NO 21
<211> LENGTH: 13
<212> TYPE: PRT
<213> ORGANISM: Artificial
<220> FEATURE:
<223> OTHER INFORMATION: peptide monomer backbone

<400> SEQUENCE: 21

Cys Ala Lys Ala Lys Ala Lys Ala Lys Ala Lys Ala Lys
1               5                   10
```

NANOCARRIER COMPOSITIONS AND METHODS

RELATIONSHIP TO PRIOR APPLICATIONS

This application is the U.S. National Phase of International Patent Application Ser. No. PCT/US10/27532, filed Mar. 16, 2010, which claims priority to U.S. Provisional Patent Application Ser. No. 61/160,575, filed Mar. 16, 2009, both of which are incorporated herein by reference in their entireties.

GOVERNMENTAL SUPPORT

The research leading to this invention was supported by NIH AI51214 to Patrick J. Sinko. Accordingly, U.S. Government has certain rights in this invention.

FIELD OF THE INVENTION

This invention relates most closely to drug delivery compositions and formulations.

BACKGROUND OF THE INVENTION

Although protein medicines have become more common with the advent of recombinant DNA technology, the pharmaceutical industry still prefers the more traditional small molecule drugs because of the poor pharmacokinetic and other properties (such as absorption, distribution, metabolism and excretion) of proteins as exogenously-administered therapeutic agents. Using proteins as therapeutic drugs, rather than small molecule mimics of these proteins, is certainly more natural and might be preferred if the aforementioned problems can be overcome.

The main problem is that proteins cannot be given orally since they are digested in the gastrointestinal tract. Even if the digestive process is suppressed, proteins alone still cannot transit from the lumen across the epithelial cell barrier into the bloodstream. Intramuscular or subcutaneous injection is the most common route of administration. Even so, most proteins have a very short half-life (measured in minutes), so the injected protein is present in the patient for only brief periods of time. A solution to this problem would be the development of orally-bioavailable protein drugs. The natural slowness of the digestive process would spread the absorption of the protein drug into the bloodstream over one or more hours, and there would be no significant obstacle to taking a pill several times each day.

The therapeutic efficacy of an orally-administered drug is dictated not only by its pharmacological properties such as potency and selectivity, but also by its biopharmaceutical characteristics such as membrane permeability and metabolic stability. In the past decade, several in-vitro and in-vivo screening techniques have been developed to assess intestinal membrane permeability of therapeutic agents as an indicator of oral absorption (e.g., B. H. Stewart, O. H. Chan, N. Jezyk, and D. Fleisher, 1997, Discrimination between drug candidates using models for evaluation of intestinal absorption, Adv. Drug Del. Res. 23:2745). The rate of intestinal absorption of a compound is critically influenced by its physicochemical properties, which in turn is dependent on its structural features. Thus, in order to gain insight into the processes involved in the intestinal transport of compounds, elucidation of solute structure/permeability relationships is essential.

The successful oral delivery of peptides and peptidomimetics poses numerous challenges. Low permeability, lack of proteolytic stability, and binding to intestinal components are some of the main factors leading to their low oral bioavailability. The proton linked intestinal oligopeptide transporter (PepT1) facilitates the apical transport of smaller peptides (i.e., typically less than 4 amino acid residues) and some peptide-like drugs (P. V. Balimane, I. Tamai, A. Guo, T. Nakanishi, H. Kitada, F. H. Leibach, A. Tsuji, and P. J. Sinko. Direct evidence for a peptide transporter (PepT1)-mediated uptake of a nonpeptide prodrug valacyclovir, Biochem. Biophys. Res. Commun. 250:246-251 (1998); A. Tsuji and I. Tamai. Carrier-mediated intestinal transport of drugs, Pharm. Res. 13:963-977 (1996); A. Tsuji, L Tamai, H. Hirooka and T. Terasaki. Beta-lactam antibiotics and transport via the dipeptide carrier system across the intestinal brush-border membrane, Biochem. Pharmacol. 36:565-567 (1987); P. J. Sinko and G. L. Amidon. Characterization of the oral absorption of beta-lactam antibiotics. II. Competitive absorption and peptide carrier specificity, J. Pharm. Sci. 78:723-727 (1989)). PepT1 is a low affinity, high capacity transporter that is involved with the absorption of relatively large doses (i.e., milligram quantities) of drugs such as the cephalosporins and penicillin antibiotics (P. J. Sinko and G. L. Amidon. Characterization of the oral absorption of beta-lactam antibiotics. II. Competitive absorption and peptide carrier specificity, J. Pharm. Sci. 78:723-727 (1989)). Larger peptides such as Leu-enkephalin, a pentapeptide, are not substrates for PepT1 and, therefore, are relatively poorly absorbed (R. T. Borchardt. Optimizing oral absorption of peptides using prodrug strategies. J. Controlled Rel. 62:23-18 (1999)). It is possible to enhance the oral absorption of low permeability, larger peptides by enhancing their stability to proteolytic degradation in the gastrointestinal (GI) tract (D. I. Friedman and G. L. Amidon. Oral absorption of peptides: Influence of pH and inhibitors on the intestinal hydrolysis of leu-enkephalin and analogues, Pharm. Res. 8:93-96 (1991); J. P. Bai, L. L. Chang, and J. H. Guo. Effects of polyacrylic polymers on the luminal proteolysis of peptide drugs in the colon, J. Pharm. Sci. 84:1291-1294 (1995); J. P. Bai, L. L. Chang, and J. H. Guo. Effects of polyacrylic polymers on the degradation of insulin and peptide drugs by chymotrypsin and trypsin, J. Pharm. Pharmacol. 48:17-21 (1996)). However, net peptide absorption remains relatively low if the effective permeability across the intestinal mucosa is also not enhanced. Using citric acid to reduce intestinal pH and minimize trypsin activity and lauroyl carnitine to enhance permeability, a significant enhancement in the oral bioavailability of a large peptide, salmon calcitonin, was achieved (Y-H. Lee, B. A. Perry, S. Labruno, H. S. Lee, W. Stern, L. M. Falzone, and P. J. Sinko. Impact of regional intestinal pH modulation on absorption of peptide drugs: Oral absorption studies of salmon calcitonin in beagle dogs, Pharm. Res. 16(8):1233-1239 (1999); P. J. Sinko, Y-H. Lee, V. Makhey, G. D. Leesman, J. P. Sutyak, H. Yu, B. Perry, C. L. Smith, P. Hu, E. J. Wagner, L. M. Falzone, L. T. McWhorter, J. P. Gilligan, and W. Stern. Biopharmaceutical approaches for developing and assessing oral peptide delivery strategies and systems: In Vitro permeability and In Vivo oral absorption of salmon calcitonin (sCT), Pharm. Res. 16(4):527-533 (1999); P. J. Sinko, C. L. Smith, L. T. McWhorter, W. Stern, E. Wagner, and J. P. Gilligan. Utility of pharmacodynamic measures for assessing the oral bioavailability of peptides. 1. Administration of recombinant salmon calcitonin in rats, J. Pharm. Sci. 84(11): 1374-1378 (1995)).

Another common strategy for improving the intestinal permeability of poorly absorbed compounds is the use of permeation enhancers that transiently modify the barrier properties of biological membranes. Despite initial enthusiasm, the invasive nature of this approach and its associated side-effects have severely hampered the use of absorption enhancers as a viable strategy for improving intestinal permeability (Hochman, J.; Artursson, P. Mechanisms of absorption enhancement and tight junction regulation. *J. Controlled Release* 1994, 29, 253-267. Citi, S.; Protein kinase inhibitors prevent junction dissociation induced by low extracellular calcium in MDCK epithelial cells. *J. Cell Biol.* 1992, 117(1), 169-178). Newer agents such as zonulin (Fasano, A.; Novel approaches for oral delivery of macromolecules. *J. Pharm. Sci.* 1998, 87(11), 1351-1356; Fasano, A. Modulation of intestinal permeability: An innovative method of oral drug delivery for the treatment of inherited and acquired human diseases. *Mol. Gen. Metabolism* 1998, 64, 12-18), that act by receptor-mediated, region-specific and reversible mechanisms displaying considerably lower cytotoxicity and systemic side-effects, now offer a promising tool in permeability enhancement. However, further studies are still necessary to fully establish their therapeutic utility.

An alternative, non-invasive approach to facilitate intestinal drug absorption is to target specific absorptive transporter systems by chemical modification of drugs to prodrugs and analogues. For instance, it has previously been demonstrated that unlike acyclovir (an anti-herpetic nucleoside), its L-valyl ester prodrug, valacyclovir, is a substrate of the intestinal proton-linked oligopeptide transporter, PepT1 (Guo, A.; Hu, P.; Balimane, P. V.; Leibach, F. H.; Sinko, P. J. Interactions of a nonpeptidic drug, valacyclovir, with the human intestinal peptide transporter (hPepT1) expressed in a mammalian cell line. *J. Pharmacol. Exp. Ther.* 1999, 289, 448454; Balimane, P. V.; Tamai, I.; Guo, A.; Nakanishi T.; Kitada, H.; Leibach, F. H.; Tsuji, A.; Sinko, P. J. Direct evidence for peptide transporter (PepT1)-mediated uptake of a nonpeptide prodrug, valacyclovir. *Biochem. Biophys. Res. Commun.* 1998, 250, 246-251). Due to the low affinity, high capacity nature of PepT1, the interaction between valacyclovir and PepT1 results in a three to four-fold increase in the bioavailability of acyclovir. Despite accepting a wide range of endogenous and exogenous substrates with peptide-like structures, PepT1, facilitates the apical transport of only di- and tri-peptides, which makes it an unsuitable target for transporting larger peptides (>5 amino acid residues) across the intestine (Amidon, G. L.; Lee, H. J. Absorption of peptide and peptidomimetic drugs. *Annu. Rev. Pharmacol. Toxicol.* 1994, 34, 321-341, Ganaphthy, V.; Leibach, F. H.; Expression and regulation of the taurine transporter in cultured cell lines of human origin. *Adv. Exp. Med. Biol.* 1994, 359, 51-57.). However, like most currently used strategies for enhancing peptide absorption, it is nonspecific or the mechanisms of action are unknown making it difficult to precisely control the resulting in vivo effect.

The foregoing comments have their counterparts in transport across the blood-brain (and other related) barriers in which endothelial cell tight junctions gate the transport from the lumen of the capillary into the tissue or organ. Various obstacles to the transport of compounds are known and impact the availability of central nervous system active agents to those with the ability to translocate across the capillary endothelium or disrupt the intercellular connections.

The advent of combinatorial chemistry has facilitated potential correlations between intestinal absorption of congeneric series of compounds and iteratively designed newer compounds and their physicochemical properties. Several groups have tried to correlate the Caco-2 cell monolayer permeability of candidate compounds with their structural attributes derived using computational techniques. Parameters such as hydrogen bonding potential, solute lipophilicity, size, charge, and conformation have been shown to be important descriptors of intestinal transport (see, for example, K. Palm, K. Luthman, A-L. Ungell, G. Strandlund, and P. Artursson, Correlation of drug absorption with molecular surface properties, *J. Pharm. Sci.* (1996) 32-39; C. A. Lipinski, F. Lombardo, B. W. Dominy, and P. J. Feeney, Experimental and computational approaches to estimate solubility and permeability in drug discovery and development settings, *Adv. Drug Del. Res.* 23 (1997) 3-25; O. S. Gudmundsson, S. D. S Jois, D. G. Vander Velde, T. J. Siahaan, B. Wang, R. T. Borchardt, The effect of conformation on the membrane permeation of coumarinic acid- and phenylpropionic acid-based cyclic prodrugs of opioid peptides, *J. Peptide Res.* 53 (1999) 383-392; K. Palm, K. Luthman, A-L. Ungell, G. Strandlund, F. Beigi, P. Lundahl, and P. Artursson, Evaluation of dynamic polar molecular surface area as predictor of drug absorption: Comparison with other computational and experimental predictors, *J. Med. Chem.* 41 (1998) 5382-5392; J. T. Goodwin, B. Mao, T. J. Vidmar, R. A. Conradi, and P. J. Burton, Strategies toward predicting peptide cellular permeability from computed molecular descriptors, *J. Peptide Res.* 53 (1999) 355-369; and E. G. Chikhale, K-Y. Ng, P. S. Burton, and R. T. Borchardt, Hydrogen bonding potential as a determinant of the in vitro and in situ blood-brain barrier permeability of peptides, *Pharm. Res.* 11 (1994) 412419.). Conventional structure-transport analyses have only explored paracellular and passive transcellular routes of diffusion.

However, very little progress has been made in the understanding of the role of structural descriptors in transporter-mediated absorption processes, primarily due to the non-availability of 3-dimensional structure of membrane transporters.

Accordingly, there is a need in the art for additional formulations for more efficient and targeted drug delivery.

SUMMARY OF INVENTION

This invention addresses these and other needs by providing a delivery system that is potentially useful for local (e.g., breast intraductal, topical), transmucosal (e.g., vaginal, nasal), direct systemic (e.g., intravenous) or oral administration.

In one aspect, the invention provides a multimeric nanocarrier for in vivo delivery of a bioactive agent, comprising at least two peptide monomers reversibly or irreversibly linked with one or more of said bioactive agents, wherein said two or more of said peptide monomers are covalently linked by a biodegradable difunctional moiety.

In certain embodiment, the biodegradable multimeric nanocarrier comprises at least two peptide monomers covalently linked by the biodegradable difunctional moiety, wherein each of said peptide monomers comprises 2-5 amino acids having functional groups in the side chains, said 2-5 amino acids in each monomer are separated from each other by respective spacers, consisting of two or more amino acids, and at least one of said functional groups is covalently bound to the bioactive agent directly or via a PEG linker.

The active group is preferably selected from the group consisting of $NH_2$, SH, COOH, —NHR and —OH, wherein R is $C_{1-4}$ lower alkyl. Thus, the amino acids having functional groups in the side chains may be independently selected from, but not limited to, the group consisting of lysine, arginine, cysteine, glutamic acid, aspartic acid, diaminobutyric acid, ornithine and homocysteine In certain embodiments, the spacers comprise amino acids lacking functional groups and without bulky side chains. Amino acids suitable for the spacers include, without limitations, beta-alanine, alanine, (gamma-amino butyric acid) GABA, glycine, short ω-amino PEG carboxylic acids and any combination thereof.

In different embodiments of the invention, the peptide monomers have identical or different amino acid sequences. Further, the peptide monomers may be identical or different with respect to the presence of PEG linkers and/or the bioactive agents linked to the monomers directly or through the PEG linkers.

In certain embodiment of the invention, the biodegradable bond formed by the biodegradable difunctional moiety is stable in an extracellular environment and is degraded within a cell. In one embodiment, this bond is a disulfide bond. In another embodiment, this bond is an ester or a carbamate bond.

In different embodiments of the invention, the bioactive agent is selected from the group consisting of imaging agents, drugs, targeting ligands, other peptide backbones, and any combination thereof.

In certain embodiments, up to 100% percent of the functional groups are bound to the bioactive agent directly or via the PEG linker. Thus, in different embodiments, 10%, 20% 30%, 40%, 50%, 60%, 70%, 80%, 85%, 90%, 95%, 99%, or 100% of the functional groups are bound the bioactive agent.

In another aspect, the invention provides a method of treating or diagnosing a disease in a mammal, preferably, human, by administering the nanocarrier according to any embodiment described above, wherein the nanocarrier provides an efficient amount of the bioactive agent to diagnose or treat the disease.

DETAILED DESCRIPTION

Unless characterized otherwise, technical and scientific terms used herein have the same meaning as commonly understood by one of ordinary skill in the art to which this invention belongs. For purposes of the present invention, the following terms are described below.

Definitions

"PEG" is used herein as an abbreviation for polyethylene glycol. PEG can have a range of molecular weights. The PEG molecular weight range contemplated for use in the present invention is from about 1000 to about 100,000 Da. PEG can be linear, branched, multi-arm, or a combination of branched and multi-arm. Various PEGs can be derivatized with various groups, such as activated ester (N-hydroxy succinimidyl ester, for example), p-nitrophenyl, aldehyde, amine, thiol, activated thiol (thiopyridine activated thiol, for example), vinyl sulfone, maleimide, aminooxy, hydrazine, tosyl, and idoacetamide. In certain other embodiments, the PEG is a 4- or 8-arm PEG. In still other embodiments, the PEG is functionalized with terminal SH groups.

"Linkers" include unsubstituted or substituted straight or branched PEGs, such as those having thiol or other functional groups suitable for attachment of an agent and/or for crosslinking.

"Nanocarrier" includes two or more peptide monomers having an agent attached.

"Agent" or "bioactive agent" includes without limitation any diagnostic, therapeutic, palliative, cosmetic and/or prophylactic compositions, including without limitation small molecules, drugs, biologicals, recombinant peptides, proteins and nucleic acids and immunochemicals, as well as diagnostic and imaging compositions, as may be further indicated by the context. In some uses, the term can relate to other types of compositions, as indicated by the context.

A biodegradable multimeric nanocarrier according to the instant invention is composed of at least 2 peptide backbone monomers (FIG. 1) linked to each other via a difunctional biodegradable moiety.

Figure 1:
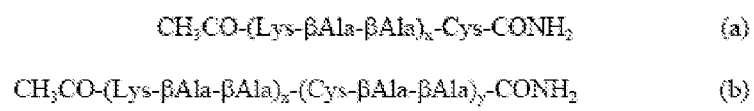
FIG. 1 is a schematic representation of a peptide backbone monomer (x=1 to 4; y=2 to 4).

The peptide monomers according to the instant invention include amino acids with functional groups in their respective side chains (functional amino acids). The functional side groups are those that can be reacted with PEGs, or bioactive agents, such as, for example, imaging agents, drugs, radioisotopes, targeting ligands or other peptide monomer backbones wherein these functional amino acids are separated by non-reactive amino acid spacers (FIG. 1). The imaging agents, drugs or targeting agents can be linked either directly on the peptide monomer backbone or through the distal ends of PEG.

Non-limiting examples of functional amino acids are Lys, which has a primary amino group, Glu or Asp which have a carboxylate group and Cys which has a thiol group. The list of suitable functional amino acids is not limited to those naturally occurring in proteins. For example, diaminobutyric acid having an amino moiety in its side chain can also be used.

Lys amino groups can be conjugated to carboxyl groups on PEG or the agent, Glu carboxylate groups can be coupled to amino groups on PEG or the agent, and Cys thiol groups can be coupled to thiopyridyl (TP) or maleimide (MAL) groups on PEG or the agent.

This multimeric nanocarrier design is also flexible so that the individual peptide monomer backbone could be used to link PEGs, bioactive agents or other peptide monomer backbones. The bioactive agents can be linked either directly on the peptide monomer backbone or through the distal ends of PEG by reversible or irreversible linkage.

To minimize potential steric hindrance to the target molecules that the nanocarrier components are designed to interact with, the functional amino acids are separated by spacers. The spacers should be long and flexible enough, the spacer amino acids should not have bulky side chains (e.g., such as the side chain in Trp, Pro or Leu) and should preferably be hydrophilic and lack reactive groups (e.g., such as those present in Thr or His). Additionally, amino acids like Tyr, Met, Ile, Phe, etc. have bulky side chains. Non-limiting examples of spacer amino acids are Gly, Ala, β-Ala, 5-amino-3-oxapentanoic acid, gamma-aminobutyric acid (GABA) and possibly, valine.

The distance between the functional amino acids is determined by spacer length. In a certain embodiment, the spacer is at least two amino acid long, but may be as long as the designer of the instant nanocarrier desires (e.g., 3, 4, 5, 6, 7, 8, 9, 10, etc). The length of the spacer depends on the size of the bioactive agent which is to be linked with the functional group. It is noted however, that generally, it would be desirable to minimize the length of the spacer, for a more efficient loading of the nanocarrier with the bioactive agent(s).

The number of the functional amino acids within the peptide monomers varies. Generally, the minimal number of the functional amino acids is two per monomer, and the maximal number is ten (i.e., the number may be 2, 3, 4, 5, 6, 7, 8, 9, or 10). Preferably, the number of the functional amino acids is between three and eight.

Thus, the peptide monomers of the instant invention may be illustrated by an exemplary formula below:

$$P\text{-}(F\text{-}(S)_m)_n\text{-}F'\text{-}P \qquad \text{Formula I}$$

wherein "F" is a functional amino acid to which an active agent is linked, either directly or through a linker such as, for example, PEG, "S" is a spacer amino acid, "P" is an optional protection group at the C- and/or N-terminus of the monomer, and "F'" is an amino acid involved in the formation of a difunctional biodegradable moiety. The values for 'm' and 'n' are provided above. Further, the functional amino acids (F) do not need to be the same. Assuming, for example, than n=3, F can be Lys, Glu, or Asp in each of the blocks (e.g., in $n_1$, F=Lys, in $n_2$, F=Glu, and in $n_3$, F=Asp).

In other embodiments, the peptide monomers may be represented by Formula II below:

$$P\text{-}(F'_1\text{-}(S)_a)_b\text{-}(F\text{-}(S)_c)_d\text{-}(F'_1\text{-}(S)_e)_f\text{-}(F\text{-}(S)_g)_h\text{-}P \qquad \text{Formula II}$$

wherein "F" is a functional amino acid to which an active agent is linked, either directly or through a linker such as, for example, PEG, "S" is a spacer amino acid, "P" is an optional protection group at the C- and/or N-terminus of the monomer, and "F'" is an amino acid involved in the formation of a difunctional biodegradable moiety. The values for a, c, e, and g are provided above, except the value of g can be zero or one if the value of h is 1. The parameters b, d, f, and h may be any integers as long as the sum of b, d, f, and h is ten or below. As has been noted with regard to the discussion of Formula I, the functional amino acids (F) do not need to be the same, and the functional amino acids (F') also do not need to be the same. Furthermore, if there are two or more functional amino acids F', the respective biodegradable bonds do not need to link the peptide monomer to the same other peptide monomer. Thus, assuming three functional amino acids F', in a peptide monomer (e.g., the first monomer) the nanocarrier of the instant invention may have one, two, or three other peptide monomers bound to the first monomer.

In another embodiment, the peptide monomers may be described as $CH_3CO\text{—}(X\text{-}Z\text{-}Z)_x\text{-}(Y\text{-}Z\text{-}Z)_x\text{—}CONH_2$, where X=Lys, Glu, Asp or diaminobutyric acid; Y=Cys, homocysteine or 1-amino-2-methyl-2-propanethiol; Z=β-Ala, Gly, Ala, or GABA (gamma-amino butyric acid); x and y are interchangeable; x is between 1 to 4; y is between 1 to 4; minimum no. of Z-spacer on the peptide backbone=2; maximum no. of Z-spacer on the peptide backbone=4.

Numerous compounds have been synthesized and used to construct peptide monomer core nanocarriers and biodegradable multimeric nanocarriers. These include SEQ ID NOs 1-8:

(Formula III)
(N-terminus) Lys-βAla-βAla-Lys-βAla-Cys (C-terminus)

(Formula IV)
(N-terminus) Lys-βAla-βAla-Lys-βAla-Cys-βAla (C-terminus)

-continued

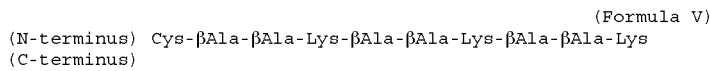
(Formula V)
(N-terminus) Cys-βAla-βAla-Lys-βAla-βAla-Lys-βAla-βAla-Lys (C-terminus)

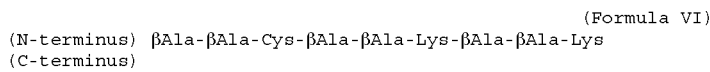
(Formula VI)
(N-terminus) βAla-βAla-Cys-βAla-βAla-Lys-βAla-βAla-Lys (C-terminus)

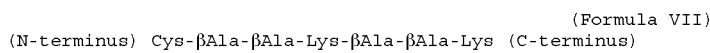
(Formula VII)
(N-terminus) Cys-βAla-βAla-Lys-βAla-βAla-Lys (C-terminus)

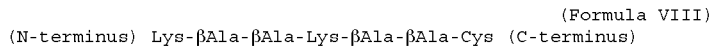
(Formula VIII)
(N-terminus) Lys-βAla-βAla-Lys-βAla-βAla-Cys (C-terminus)

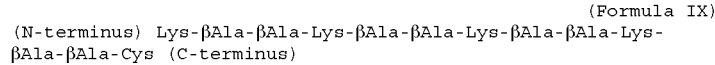
(Formula IX)
(N-terminus) Lys-βAla-βAla-Lys-βAla-βAla-Lys-βAla-βAla-Lys-βAla-βAla-Cys (C-terminus)

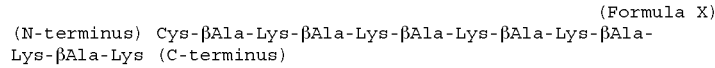
(Formula X)
(N-terminus) Cys-βAla-Lys-βAla-Lys-βAla-Lys-βAla-Lys-βAla-Lys-βAla-Lys (C-terminus)

As noted above, the linkage occurs via biodegradable bonds whereby a difunctional biodegradable moiety is formed, as discussed in details below.

Figure 3:
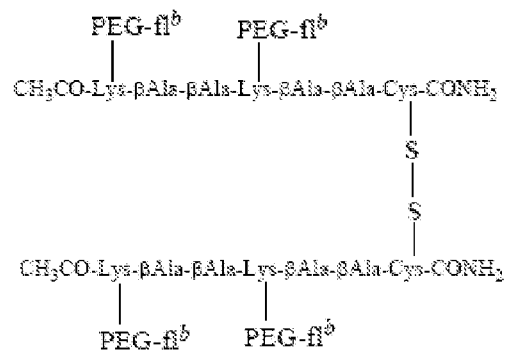
FIG. 3 shows an exemplary structure of a singly labeled (fluorescein) homodimeric peptide backbone PEG nanocarrier.
Figure 4:
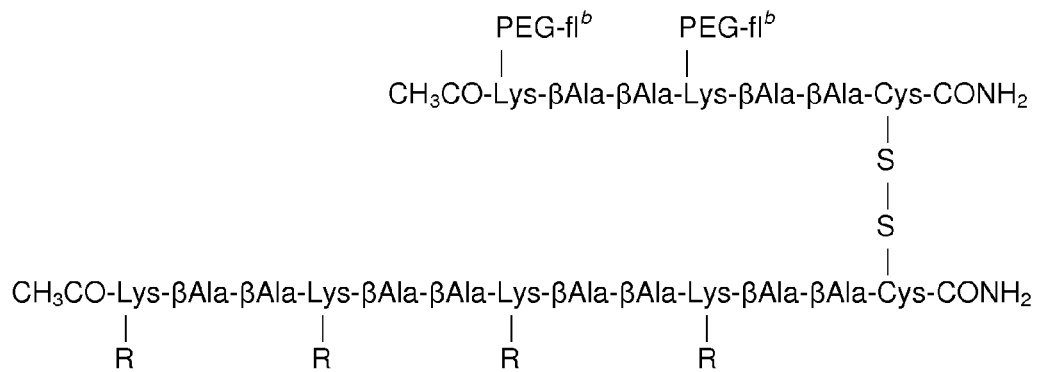
FIG. 4 shows an exemplary structure of a doubly labeled (fluorescein and Texas Red) heterodimeric peptide backbone PEG nanocarrier.

Preferably, such biodegradable bond is programmable, i.e., it is stable in one set of conditions and is predictably disrupted under another set of conditions. For example, the disulfide bond (i.e., the difunctional biodegradable moiety of "—S—S—") of certain embodiments of the multimeric nanocarrier is stable in blood but unstable after the nanocarrier has entered into the cytosol of a cell. Cys on one peptide backbone monomer forms a disulfide bond with Cys-S-thiopyridine of another peptide backbone monomer to form the nanocarrier (in case of biodegradable multimeric nanocarrier). Cys can be replaced by another thiol amino acid (such as homocysteine) or more sterically hindered 1-amino-2-methyl-2-propanethiol to obtain a more stable disulfide bond in comparison to the free Cys counterpart in the nanocarrier (FIGS. 3, 4).

Another example of a biodegradable nanocarrier incorporates one or more ester or carbamate bonds. Upon degradation, the nanocarrier yields individual peptide backbone monomers with predictable (and hence, programmable) bio-elimination properties.

In certain embodiments, the overall nanocarrier has the advantage of minimizing polydispersity since the attachments of multiple copies of relatively short PEG onto the peptide backbone monomers can be obtained stoichiometrically with low polydispersity.

The multimeric nanocarrier can be either homodimeric or heterodimeric. Homodimeric nanocarrier is constructed by linking 2 peptide backbone monomer units, each unit carrying identical copy numbers of either PEGs, drugs, imaging agents or targeting ligands, for example, linking a 2-copy peptide backbone monomer with another 2-copy peptide backbone monomer each carrying same type of imaging agent (FIG. 3).

Figure 2:
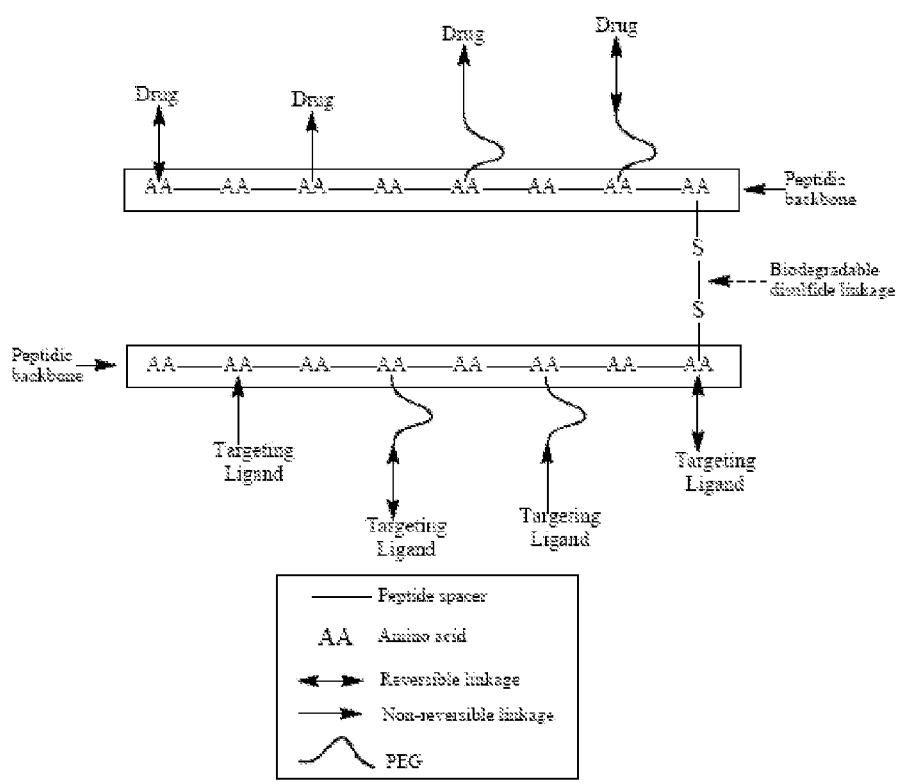
FIG. 2 is a schematic representation of a monodisperse biodegradable multimeric nanocarrier composed of a peptide backbone irreversibly or reversibly conjugated with one or more targeting ligands and drugs either directly or through the distal ends of PEG.

Heterodimeric nanocarrier is constructed by linking 2 peptide backbone monomer units, each unit carrying different moieties of either PEGs, drugs, imaging agents or targeting ligands, for example, linking a 2-copy PEGylated peptide backbone monomer with a non-PEGylated peptide backbone monomer each carrying different types of imaging agents (FIG. 4). The programmable biodegradable bonds shown in FIGS. 2, 3 and 4 are disulfide bonds. The biodegradation of disulfide bond can be prolonged by replacing Cys with sterically hindered Cys analogues (FIGS. 3, 4).

Non-limiting examples of two peptide monomers are illustrated in formulae XI and XII below:

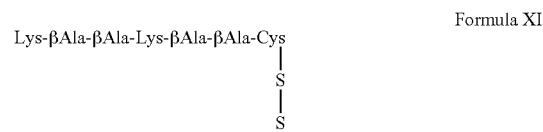
Formula XI

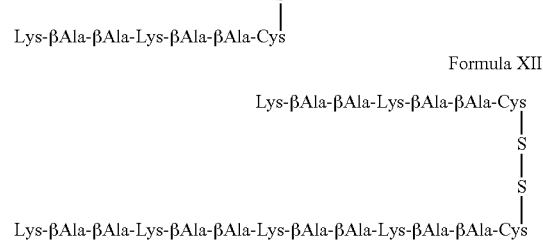
Formula XII

In the processes of making compounds of formulae III-XII above, PEG attachment was performed on Lys or Cys. The bioactive agents (targeting agents, drugs, imaging agents) were either directly attached to the peptidic core or on the distal ends of the PEGs that are directly attached to the peptidic core. The N-terminus was either acetylated or labeled. The peptidic cores in examples 9 and 10 were directly dimerized (homodimerization or heterodimerization) via the Cys moieties. The dimerization can also be achieved by homofunctional or heterofunctional PEGs linking to the peptidic cores. Drugs (ritonavir, amprenavir), targeting groups (e.g., DV3, fMLF, mannose), and biological modifiers (e.g., R.I. Tat-9) have been used in the construction of various nanocarriers.

In accordance with any of the above embodiments, the invention further comprises an agent. In certain embodiments, the agent is a drug and may be selected from the group consisting of antiinflammatory drugs including: non-steroidal anti-inflammatory drugs (NSAID) and NSAID analogs, indomethacin, sancycline and sancycline analogs, olvanil and olvanil analogs, retro-olvanil and retro-olvanil analogs, olvanil carbamate, NSAID-ache, budesonide and budesonide analogs, methylprednisolone and methylprednisolone analogs and dexamethasone and dexamethasone analogs. Also envisioned is the use of Anticancer drugs such as camptothecin, carboplatin, doxorubicin, paclitaxel, bleomycin; anti-HIV drugs including protease inhibitors (non-limiting examples: saquinavir, amprenavir, ritonavir, indinavir, nelfinavir, tipranavir, darunavir and atazanavir) reverse-transcriptase inhibitors, integrase inhibitors viral entry inhibitors (e.g. enfuvirtide) and monoclonal antibodies.

In certain other embodiments, the bioactive agent is an imaging agent. Suitable non-limiting examples of imaging agents include coloring dyes like FD and C dyes, or visible/near infrared fluorescence dyes like fluorescein, methylene blue, rhodamine, dansyl, Alexa, cyanine dyes, Hilyte, Texas Red, indocyanine green and the like.

In certain embodiments, the agent is coupled to the PEG by a linking group selected from the group consisting of peptide linkers, self-immolative linkers, acid sensitive linkers, bifunctional organic linking agents, bifunctional inorganic crosslinking agents, Leu-Gly, Glu(Leu-Gly)$_2$, Arg-Gly-Asp-Cys, Gly-Arg-Gly-Asp-Ser, Gly-Arg-Gly-Asp-Ser-Pro, cyclic Arg-Gly-Asp-Tyr-Lys, or any peptide with Arg-Gly-Asp. In certain embodiments, the doxorubicin is coupled to the PEG by a linker selected from the group consisting of Leu-Gly, Glu(Leu-Gly)$_2$, Arg-Gly-Asp-Cys, Gly-Arg-Gly-Asp-Ser, Gly-Arg-Gly-Asp-Ser-Pro, cyclic Arg-Gly-Asp-Tyr-Lys, or any peptide with Arg-Gly-Asp.

The agent may also be a cell uptake promoter, transporter, receptor, binding or targeting ligand. Suitable examples of these agents categories include, without limitations, a vitamin such as, but not limited to, biotin, pantothenate, vitamin B6, or vitamin B12, or analogs thereof. It may also be a carbohydrate for which a transporter exists, such as for glucose and glucose derivatives. It may also be a chemotactic peptide such as a formyl-methionyl peptide. Examples of other peptide targeting agents with a range of size and amino acid order includes the peptide formyl-methionyl-leucyl-phenylalanine (fMLF) peptide and variants thereof which serves as a transport enhancing moiety and increases drug delivery into cells expressing the receptor for that peptide. fMLF is only one example of the class of formyl-methionyl peptides that binds to this receptor. Other examples include other formylmethionyl peptides and proteins capable of binding to the formyl peptide receptor on the surface of phagocytic cells, which also has been reported to bind to certain other, unrelated peptides lacking the formylmethionyl moiety, and these latter peptides unrelated to formylmethionyl peptides but capable of binding to the receptor are fully embraced herein. Other transport enhancing moieties may include Tat-biotin, retro-inverso (RI)-Tat, and RI-TAT-biotin. It may be a chemokine, such as RANTES, SDF-1α, or IL-2. It may also be a peptide such as Tat, penetratin or VEGF, or a membrane fusion peptide such as gp41. It may also be an enzyme such as neuramimidase. It may be an antibody or an antibody fragment with specific affinity for lymphocyte subpopulations, neurons or other cell types. Examples of such antibodies include antibodies to CD4, which may target helper T-cells, or CD44, which may target ovarian cancer cells. It may also be an antigen or epitope such as influenza virus hemagglutinin. It may also be a hormone such as estrogen, progesterone, or growth hormone. It may also be an adhesion molecule such as ICAM, NCAM or a lectin. It may also be a lipid, such as myristic acid or stearic acid. It may be an oligonucleotide or an antisense oligonucleotide such as aptamers containing 5-(1-pentyl)-2'-deoxyuridine. These are merely non-limiting examples. Any of the cell uptake promoters embraced herein may be provided as a form which is capable of being covalently attached to a polymer or therapeutic agent as described above, such as through a functional or reactive group on the cell uptake promoter or by a chemical modification to provide one.

Cell uptake promoter peptide comprises a Tat-inhibitory polypeptide, comprising an amino acid sequence of: R-Arg-Lys-Lys-Arg-Arg-Gln-Arg-Arg-Arg-X-(biotin)-Cys-NH$_2$, and biologically and pharmaceutically acceptable salts thereof, stereo, optical and geometrical isomers thereof, including retro-, inverso and retro-inverso analogues, where such isomers exist, as well as the pharmaceutically acceptable salts and solvates thereof, wherein R comprises the residue of a carboxylic acid or an acetyl group; and X is a Cys or Lys residue.

The bioactive agent of the instant invention may also be a diagnostically useful compound that may be bound via a functional group thereon to the composition of the invention. Diagnostic moieties having reporter molecules that can be detected by imaging equipment may include radioactive, paramagnetic, fluorescent or radiopaque chemical entities. Specific examples include iodinated sugars that are used as radiopaque agents, and can be appended to linker backbones using ester or other linkages as described above. Additional diagnostic examples include the use of radioactive metal complexes such as Technetium-99m in coordination compounds such as types of, e.g. $^{99m}$Tc-Tetrofosmin or $^{99m}$Tc-Sestamibi, which are used in various types of scintigraphic imaging.

By adjusting the copy number of both the therapeutic or diagnostic agent and the cell uptake promoter on the selected polymer, and the environment of the reducible disulfide bond between the therapeutic or diagnostic agent and the polymer, the pharmacokinetics, transport and delivery properties of the conjugate may be selected for a particular target cell type, persistence of the conjugate in transit or terminal bodily compartments, particular reducing environment which frees the active therapeutic or diagnostic agent, among other parameters, can be selected to maximize the therapeutic or diagnostic value of the conjugate for its particular utility. The skilled artisan, by the guidance provided herein, will be able to prepare and administer a composition of the invention for the desired end use.

In accordance with any of the above embodiments, the invention further comprises a surface modification. In certain embodiments, the surface modification alters a property selected from the group consisting of surface charge, surface charge density, surface hydrophobicity, and surface charge and hydrophobicity combined. In certain embodiments, surface modifications will affect body, tissue, organ and cell interactions, as well as distribution and persistence of the nanocarrier of the instant invention.

For example, the reaction of 2-methoxyethanethiol with the nanocarrier results in a neutral surface charge with an exposed methoxy (OMe) group and the reaction of 1,2-Ethanedithiol results in a negative surface charge with an exposed —SH group and so on.

To increase the hydrophobic surface character, a series of increasingly hydrophobic amino acids (i.e., Gly, Ala, Val, Leu, norleucine (NLE)) may be covalently linked to the PEG linker using mercaptoethanol. Each of these amino acids has one addition $CH_3$ group adding approximately ¹A log unit additional hydrophobicity than the previous amino acid in the series (incremental Hansch π value=0.5 per $CH_3$ group).

To modify both the surface charge and hydrophobic interaction, hydrophobic and hydrophilic amino acids (e.g. Gly, Ala, Asn, Gln, Ser) are attached using agents such as mercaptoethanol.

In accordance with any of the above embodiments, the invention further comprises a targeting moiety. In certain other embodiments, the targeting moiety is a peptide. In certain other embodiments, the peptide is an RGD peptide. Additionally, amino acid sequence CLPVASC and CGAREMC are kidney-specific targeting moieties, while sequences CNSRLHLRC, CENWWGDVC, WRCVLREG-PAGGCAWFNRHRL are brain-specific targeting moieties. U.S. Patent Pub. 20050037417 (Ruoslahti).

Moreover, it would be desirable that the peptide monomers of the instant invention contain orthogonal functional groups, such that the number of substituent groups on the polymer can be specified and well controlled during manufacturing. Also, by controlling the addition of appended groups to one or more specific functional groups on the polymer backbone, a monodisperse product, defined as a population of molecules having the same molecular mass, may be readily achieved. By definition, the term "orthogonal" refers to chemical groups that can be involved in specific chemical reactions independently of one another. By way of non-limiting examples, when working with peptides, the two most commonly used orthogonal groups are the amino group (—NH$_2$) and the thiol group (—SH). Reagents are available that will react with only amino groups or only thiol groups, but not with both. In manufacturing a particular conjugate, one may begin with a scaffold that contains amino and thiol groups, each present in integer numbers. The peptide monomer may have a sequence such as Lys-Cys-Cys-Cys, separated by the appropriate spacers which have been omitted for simplicity. The amino acid Cys has a thiol group, so this peptide can react with 3-molar equivalents of a thiol specific reagent, such as maleimide-PEG to give the product: Lys-Cys(PEG)-Cys(PEG)-Cys(PEG) where by convention the thiol and maleimide groups are understood to be present but not specifically written.

The amino acid Lys has one amino group on the side chain, but there is one amino group present due to the peptide backbone structure (i.e., the N-terminus). Thus, the amino acid Lys has two amino acid groups; the α-amino group which would be the N-terminus and the ε-amino group on the side chain. Therefore, this peptide can react with two equivalents of an amino group specific reagent, such as the N-hydroxysuccinimide activated ester of biotin to give: (biotin)Lys(biotin)-Cys(PEG)-Cys(PEG)-Cys(PEG) where by convention, the biotin due to react the peptide backbone structure is written at the extreme left and the biotin associated with the Lys is written in parentheses. Thus, a peptide acting as a scaffold of the formula: (Lys)$_n$-(Cys)$_m$ can be derivatized using two orthogonal reactions to give a product with exactly n+1 copies of the amine-reactive chemical and m copies of the thiol-reactive chemical. By being orthogonal, these 2 reactions can be carried out with either the thiol or the amino reaction first and without regard to any significant improper cross-reaction occurring.

An additional methodology is to use orthogonal protecting groups, such as in the peptide: Cys(t-butyl)-Cys(trityl)-Cys(trityl). All 3 thiol groups in this peptide are blocked from reacting with thiol-specific reagents. However, treatment with reducing agent (e.g. dithiothreitol at pH 8) will remove the t-butyl group to give: Cys-Cys(trityl)-Cys(trityl) which may be reacted with maleimide-PEG to give: Cys(PEG)-Cys(trityl)-Cys(trityl). Then treatment with acid will remove the trityl group to give: Cys(PEG)-Cys-Cys which may be reacted with maleimide-biotin to give: Cys(PEG)-Cys(biotin)-Cys(biotin).

The acid treatment and dithiothreitol treatment may be performed in the reverse order. This peptide still has an amino group available, such as for reacting with amine-reactive fluorescein isothiocyanate to give: (fluorescein)-Cys(PEG)-Cys(biotin)-Cys(biotin). Similarly, the Fmoc and tBoc protecting groups for amines are orthogonal in that the first is base-labile and the second is acid-labile, such as in the peptide: (Fmoc)Lys(tBoc)-Cys(t-butyl)-Cys(trityl) which can accommodate 4 separate reactions.

For Lys, methyltrityl (Fmoc-Lys(Mtt)) and 1-(4,4-dimethyl-2,6-dicyclohex-1-ylidedene)ethyl, (Fmoc-Lys(Dde)) derivatives can also be used for orthogonal synthesis where Mtt is cleavable with weak acid conditions, Dde is cleavable using hydrazine, and Fmoc is base labile. Further, Fmoc-Lys(Mtt) is orthogonal Fmoc-Lys(Dde) is semi-orthogonal protecting group combinations but they are both useful.

Of course, the combination of orthogonal functional groups and orthogonal protection groups is also envisioned.

PEG linkers, in various embodiments, can be complexed with one or more agents, such as a therapeutic or imaging agents, can be crosslinked with itself or another compound, crosslinked and aggregated, crosslinked and complexed with an agent, or crosslinked and aggregated and complexed with an agent.

Suitable PEG linkers include PEG polymers, block polymers, block copolymers and copolymers include, without limitations PEG polymers with thiol groups—Materials containing PEG polymer with multiple thiol terminus groups can serve as PEG scaffolds. Suitable materials include PEG having a molecular weight in the range of about 1,000 to about 100,000 Da, with more than 2 thiol groups. Multi-arm PEG and branched PEG are suitable as scaffolds, including multi-arm PEG having 2-, 3-, 4-, or 8-arms, where two or more or even all of the arms have a thiol group. In some embodiments, the thiol group will be unbound, and available for replacement of the hydrogen with another group, in other embodiments, the thiol group can have a different group bound to it that is replaced with a desirable group during complexation, crosslinking, or some combination of the two. In one preferred embodiment, a multi-arm thiol-terminated PEG linkers such as the 4-arm or 8-arm thiol PEG is presented. The central portion can include a central junction with PEG moieties, linked to the central portion with ether linkages, or other suitable linkages, and terminating in a thiol group for at least some of the PEG moieties.

In some embodiments, multiple thiol groups can be achieved by branching a linear PEG, or by branching a multi-arm PEG, and terminating at least a portion of the branch PEG units with a thiol group. Through branching or a combination of branching and use of multi-arm PEG, the number of thiol groups desired, such as 2, 3, 4, 8, or more can be achieved.

In some embodiments, such as in the use of a multi-arm PEG attached to agents having low solubility, such as an agent that is sparingly or slightly soluble, attachment of additional agents to the PEG linker results in only a limited effect on the solubility of the nanocarrier achieving adequate water solubility and, at the same time, a therapeutically relevant drug dose. In addition bioadhesive targeting can be combined by selection of additional groups to attach to the PEG linker, such as the use of Leu-Gly or Arg-Gly-Asp as a linker for the bioactive agent to the PEG linker.

The nanocarrier of the instant invention may be formulated according to methods well known in the art. Briefly, the formulation comprises the nanocarrier according to any embodiment described above and a pharmaceutically acceptable carrier, as well as any desired excipients. For example, the formulations in the liquid form may comprise physiologically acceptable sterile aqueous or nonaqueous dispersions, suspensions or emulsions and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil), and injectable organic esters such as ethyl oleate.

The nanocarrier formulations may also contain adjuvants, such as preserving, wetting, emulsifying, and dispersing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of an injectable pharmaceutical form can be brought about by the use of agents delaying absorption, such as aluminum monostearate and gelatin.

Solid dosage forms for oral administration of the nanocarrier include capsules, tablets, pills, powders, and granules. In such solid dosage forms, the nanocarrier is admixed with at least one of the following: (a) one or more inert excipients (or carrier), such as dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid application forms include emulsions, suspensions, syrups, and elixirs. In addition to the active compounds, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Ultimately, the choice of the formulation depends on the route of administration of the nanocarrier formulation, which, in turn, may depend on the disease or a condition which is to be treated, prevented or diagnosed. Thus, in another aspect, the invention provides a method of treating, preventing and/or diagnosing a disease or condition, comprising administering to an animal or human in need thereof a composition comprising the nanocarrier according to any embodiment of the invention, wherein the nanocarrier comprise an amount of the agent sufficient to treat, prevent and/or diagnose the disease or condition.

Depending on the disease or condition, the envisioned administration routes include oral, intravenous, intraarterial, intramuscular, intracolonic, intracranial, intrathecal, intraventricular, intraurethral, intravaginal, sub-cutaneous, intraocular, topical, intranasal, and any combinations thereof.

The invention will now be described in the following non-limiting examples.

EXAMPLES

PEGylation, the process of conjugating proteins and other drugs to poly(ethylene glycol) (PEG), has improved the clinical performance of drugs such as interferon α-2a (PEGASYS®) and interferon α-2b (PEGINTRON®) for treating diseases such as Hepatitis C infection and chronic myelogenous leukemia. The observed improvements in clinical efficacy are primarily due to reduced proteolytic degradation, enhanced physical stability, higher solubility, and reduced systemic clearance due to a longer circulating half-life. PEGylation results in reduced immunogenicity and antigenicity as well as reduced toxicity by, among other mechanisms, reducing interactions with cells of the immune system such as dendritic cells and macrophages. These are the very same cells that are infected by the Human Immunodeficiency Virus (HIV). Therefore, while PEGylation has been enormously successful in maintaining plasma concentrations of various drugs, its utility as a targeting agent or drug delivery scaffold for eradicating HIV infection is low. Since many anti-HIV drugs have poor physicochemical and biopharmaceutical properties, the inventors concentrated on designing nanocarriers capable of delivering drugs specifically to HIV infected cells while improving the solubility, stability and pharmacokinetics of these potent drugs.

Initially, the inventors developed a series of multi-arm and branched PEG nanocarriers containing multiple copies of the chemo-attractant peptide N-formyl-Met-Leu-Phe (fMLF) for the specific purpose of promoting macrophage uptake. Maximal uptake in macrophage-like differentiated human U937 cells occurred at a scaffold size of 20 kDa whereas further increases in molecular weight up to 40 kDa resulted in lower uptake. Similar results were also observed in vivo. However, virtually no uptake was observed when fMLF was not present on the PEG nanocarrier consistent with reports of reduced interactions with macrophages due to PEG.

Polymer shape and branching are also known to alter the properties of PEG carriers. For example, a branched PEG constructed of two linear molecules of succinimidyl carbonate PEG attached to the α and ε-amino groups of lysine demonstrated higher proteolytic stability and a longer half-life in the blood as compared to their native and linear polymer conjugate counterparts. The binding of a branched 10 kDa PEG to asparaginase reduced antigenicity by 10-fold as compared to the counterpart with a 5 kDa linear PEG. It was also found to reduce uricase immunogenicity and antigenicity more efficiently than the linear 5 kDa polymer. While the 10 kDa PEG2 is considerably smaller than the glomerular filtration threshold size, it was found to accumulate to a significant extent in the liver of Balb/c mice suggesting that molecular shape and volume may be important factors in determining the biodistribution and clearance pathways of PEG nanocarriers.

Notably, the majority of the prior studies are focused on the initial body distribution of the nanocarriers. In contrast, in the present study, the inventors shift focus from the initial body distribution of nanocarriers (i.e., actively targeting HIV-infected cells) to designing nanocarriers with preprogrammed body elimination properties (i.e., nanocarriers that selectively release their cargo inside cells, degrade and follow a predetermined systemic elimination pathway).

The materials and methods described below apply to all of the examples unless specified otherwise.

Materials: 2-arm peptidic core [Acetylated-Lys-βAla-βAla-Lys-βAla-βAla-Cys(TP)-Amidated MW 813 Da], 4-arm peptidic core [Acetylated-Lys-βAla-βAla-Lys-βAla-βAla-Lys-βAla-βAla-Lys-βAla-βAla-Cys(TP)-amidated MW 1317 Da] and 6-arm peptidic core [Fmoc-Cys(t-Butyl-thio)-βAla-Lys-βAla-Lys-βAla-Lys-βAla-Lys-βAla-Lys-βAla-Lys-Amidated MW 1627 Da] were purchased from W.M Keck Foundation Biotechnology Resource Laboratory (New Haven, Conn.). Fluorescein-PEG5 kDa-NHS and m-PEG3.4 kDa-NHS were purchased from Nektar Therapeutics Corp. (Huntsville, Ala.). Texas Red-NHS was obtained from Invitrogen (Eugene, Oreg.). Sodium phosphate monobasic, sodium phosphate dibasic, tris buffer, dithiothreitol (DTT), 2,2'-dithiodipyridine (Aldrithiol-2; TP-TP), glutathione (GSH), ninhydrin, phenol, phenylalanine, potassium cyanide, trifluoroacetic acid (TFA) and dimethyl sulfoxide (DMSO) were purchased from Sigma-Aldrich Corp. (St. Louis, Mo.). Dimethylformamide (DMF) was purchased from Acros Organics (Morris Plains, N.J.). Centrifugal filters (Amicon Ultra 30 kDa and Microcon 10 kDa) were obtained from Millipore Corp. (Billerica, Mass.). DIEA (N,N'-Diisopropylethylamine) was purchased from Acros Organics (Geel, Belgium).

Spectral Analyses: UV spectra were recorded on a Beckman Coulter DU 640 spectrophotometer. Mass spectrometry using matrix-assisted-laser-desorption-ionization time-of-flight (MALDI-TOF) was performed on Voyager 4800. MALDI/MS data fully confirmed the structure of compounds.

Chromatography: Gel permeation chromatography was performed on a Sephadex G-75 (Amersham Bioscience; Uppsala, Sweden) using phosphate buffers (PB) pH 5.5±0.2 and 7.4±0.2 as eluents. The fluorescence readings of each fraction obtained from gel permeation chromatography were detected at $E_x$=485 nm and $E_m$=535 nm (for fluorescein) using a Tecan GENios microplate reader (Durham, N.C.). Fluorescent compounds were also subjected to HPLC (Waters 2475 Multi λ Fluorescence Detector) using a size exclusion chromatographic column, TSKgel G4000PW×1, 7.8 mm×30 cm, 10 μm (Tosoh Bioscience; Montgomery Ville, Pa.).

Figure 5:
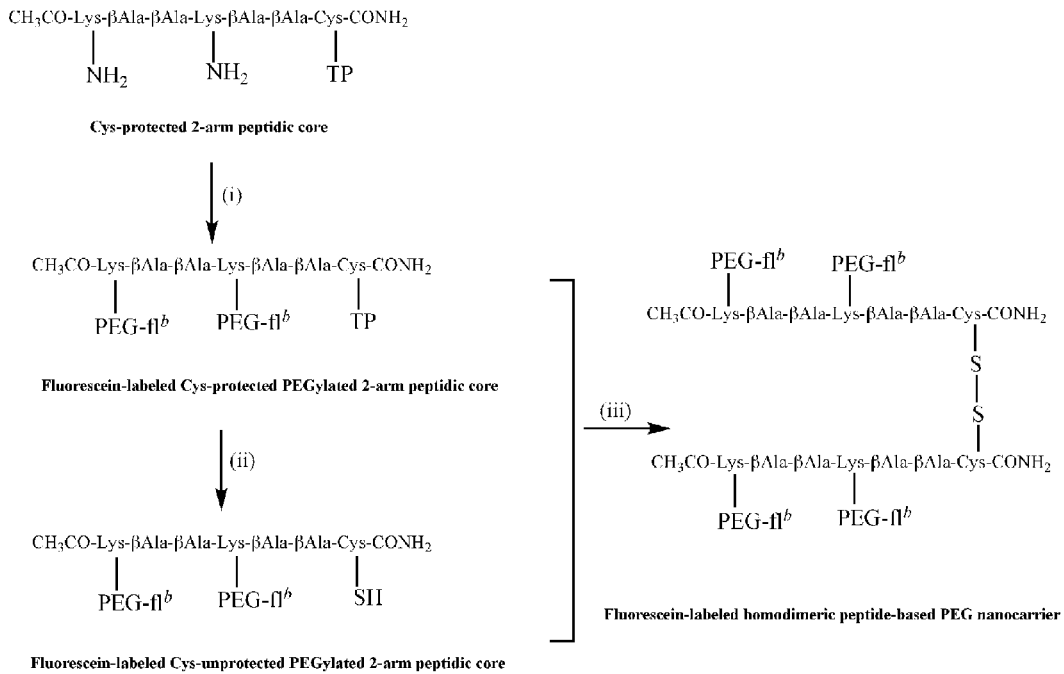
FIG. 5 is a schematic illustration of synthesis of homodimeric peptide-based PEG nanocarrier.
Figure 6:
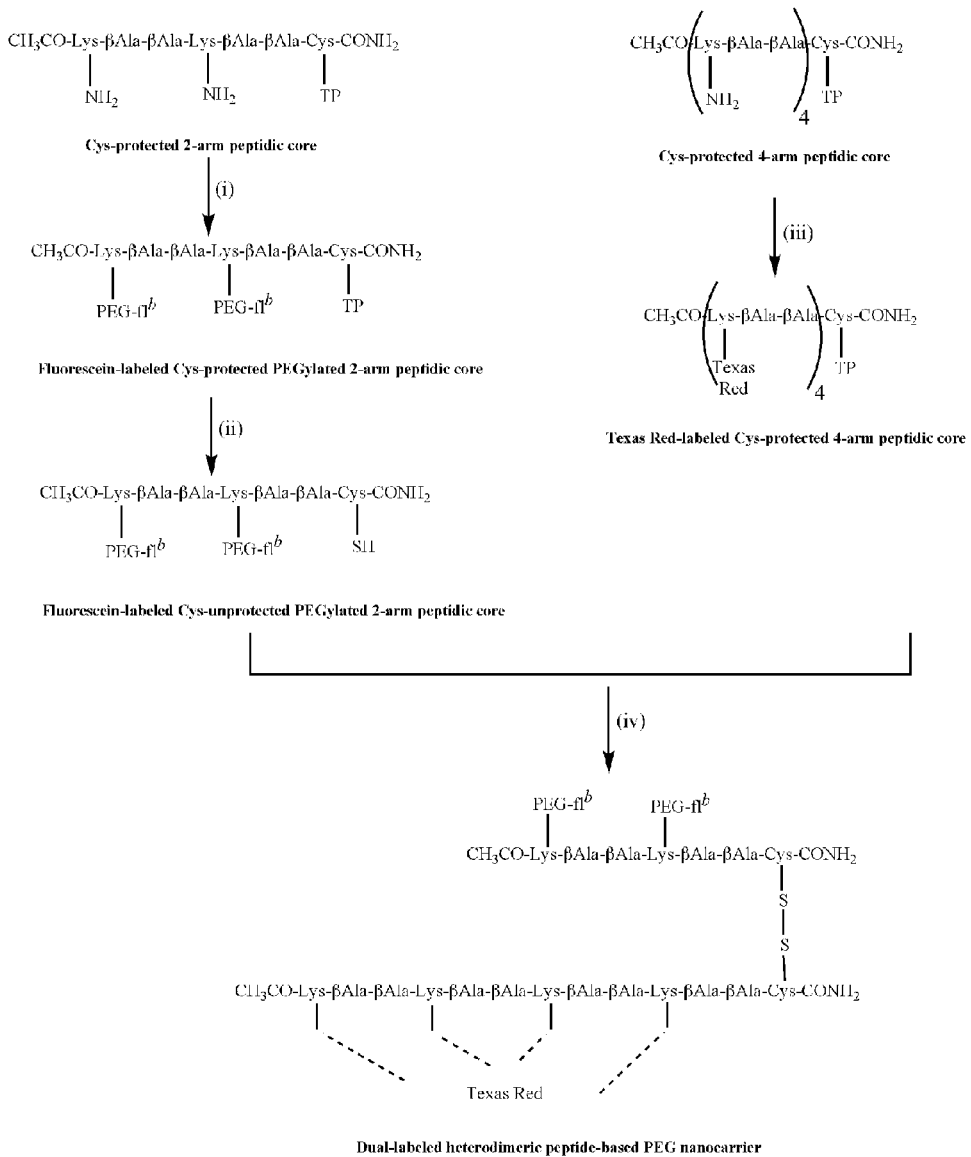
FIG. 6 is a schematic illustration of synthesis of heterodimeric peptide-based PEG nanocarrier.
Figure 7:
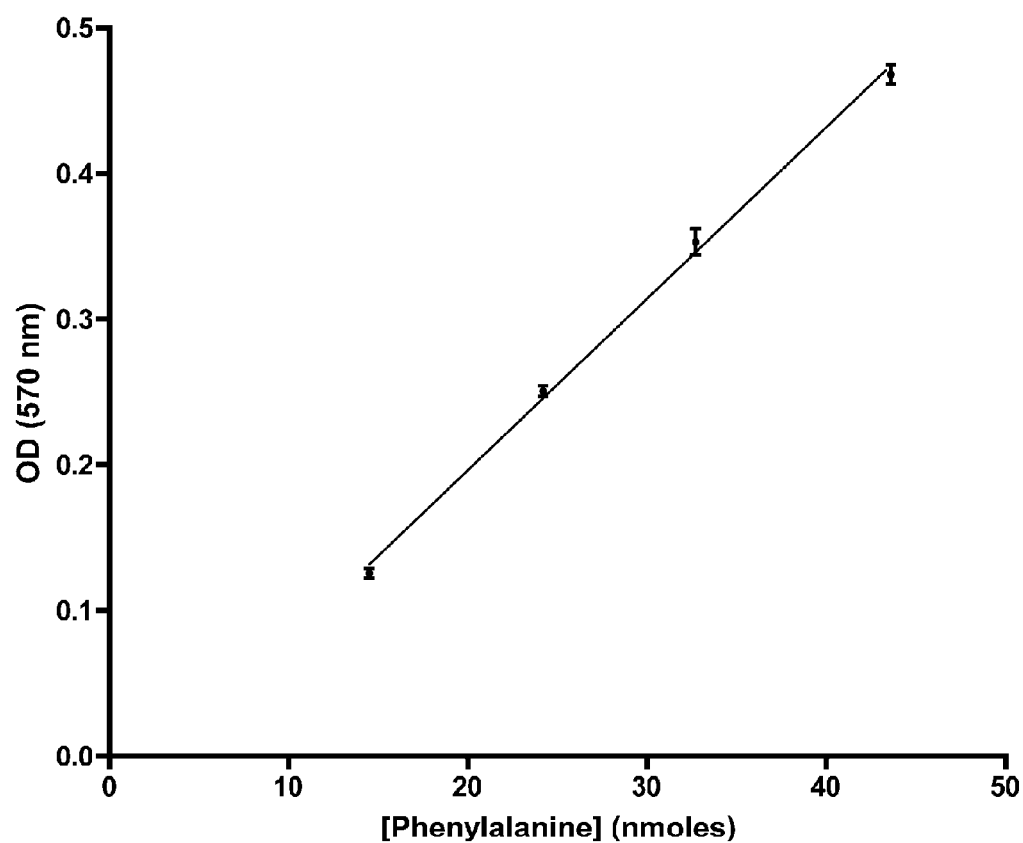
FIG. 7 is a calibration curve of primary amine group of phenylalanine as a function of optical density (570 nm). This curve was obtained from quantitative Kaiser chromogenic assay. The concentration of primary amine groups on the 2-, 4- and 6-arm peptidic cores was determined using this chromogenic assay. All measurements were done in triplicate. ($R^2=0.993$)

Quantification of peptidic cores: Nanocarriers were prepared using PEGylated and non-PEGylated peptidic cores (FIGS. 2, 5 and 6). The concentrations of free E-amine groups of lysines on the peptidic cores were calculated using a quantitative Kaiser chromogenic assay established by Sarin et. al with modifications. The standard curve was first generated with phenylalanine. Ninhydrin solution (6% w/v) in ethanol was added to various concentrations of phenylalanine solution (14.5-60 nmoles) dissolved in double distilled water, followed by the addition of phenol (4 g/ml) and potassium cyanide (0.65 mg/ml). The mixtures were heated at 110° C. for two minutes, followed by the addition of 2 ml of 60% ethanol. Optical density was read at 570 nm and a standard curve was prepared (FIG. 7). DMSO was used to dissolve the 2-arm peptidic core (2 free amino groups on lysine) since it was sparingly soluble in water. The 4-arm peptidic core (4 free amino groups on lysine) and 6-arm peptidic core (6 free amino groups on lysine) were freely soluble in water. The concentrations of each of the peptidic cores were determined using the phenylalanine standard curve.

Figure 8:
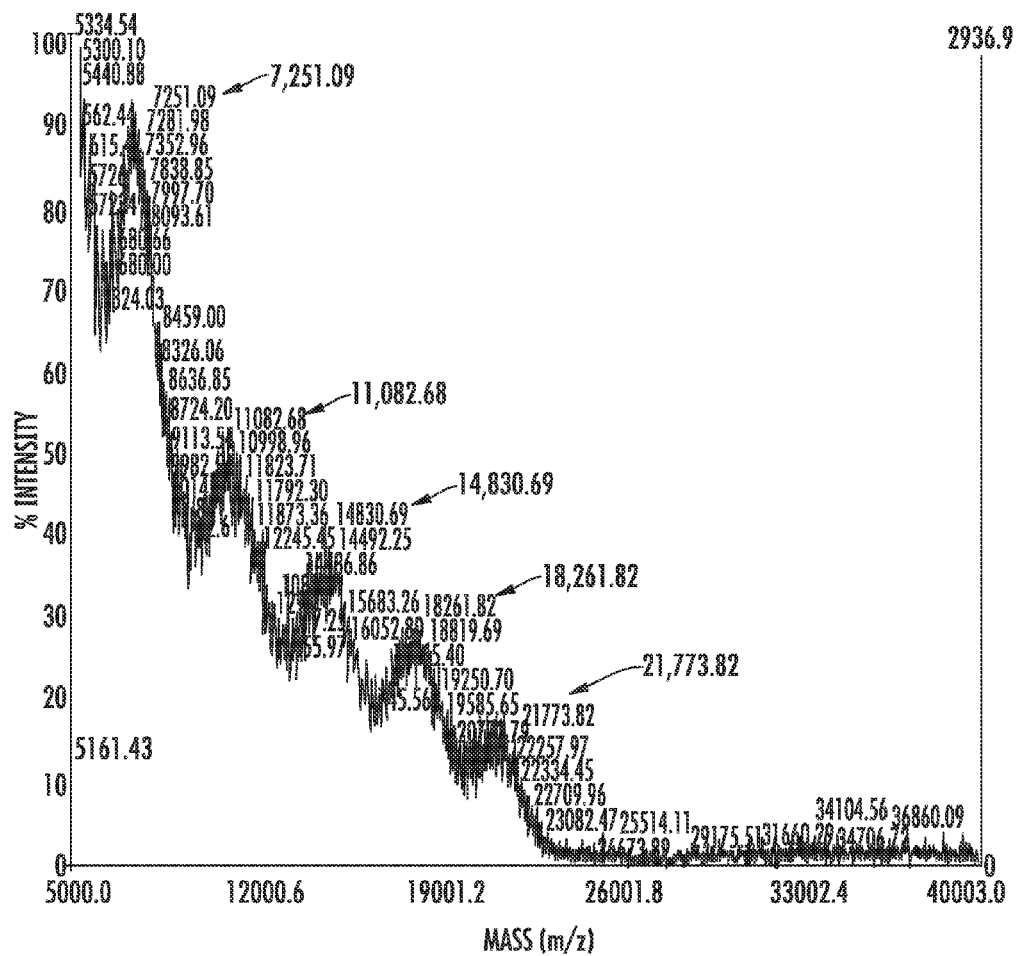
FIG. 8 is a MALDI-TOF (m/z) spectrum of crude 6-arm PEGylated peptidic core reaction, showing the heterogeneity of products. The products contain a mixture of conjugation of 2 (7251 Da), 3 (11,082 Da), 4 (14,830 Da), 5 (18,261 Da) and 6 (21,773 Da) copies of m-PEG3.4 kDa.

PEGylated 6-arm peptidic core: The PEGylation reaction of the peptidic core with 6 possible attachment sites (6-arm) at lysines was performed with 3 molar excess of m-PEG3.4 kDa-NHS. This reaction was carried out overnight using DMF:DIEA (99:1). The crude PEGylated 6-arm peptidic core reaction was analyzed using MALDI-TOF (FIG. 8).

Figure 9:
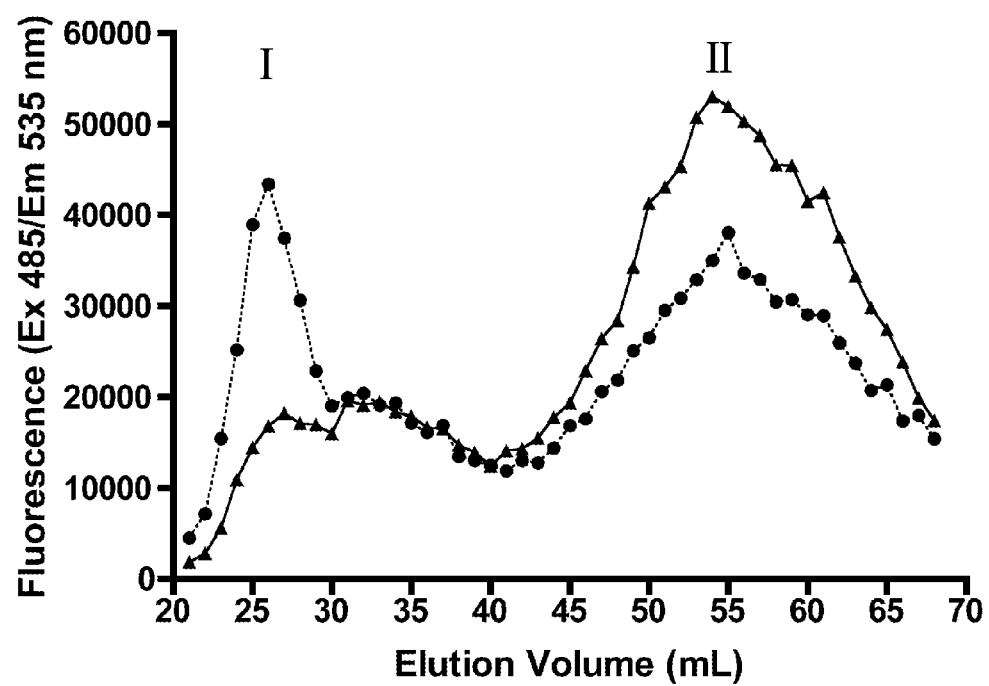
FIG. 9 is a gel permeation chromatogram showing preparation of labeled 'Cys-protected fully PEGylated 2-arm peptidic core' from labeled 'Cys-protected partially PEGylated 2-arm peptidic core' and unreacted fluorescein-PEG5 kDa using Sephadex G-75 column in 100 mM phosphate buffer pH 7.4±0.2. The fluorescence measurements of each elution volume was detected at $E_x$=485 nm; $E_m$=535 nm corresponding to the fluorescein dye. PEGylation reaction on the 2-arm peptidic core was carried out in two different reaction conditions (a) DMSO: 100 mM phosphate buffer pH 7.4±0.2 (3:7) (black triangles, ▲) (b) DMSO: 100 mM phosphate buffer pH 7.4±0.2 (7:3) (black circles, ●), where peak I indicates Cys-protected 'fully' PEGylated 2-arm peptidic core and peak II indicates a mixture of Cys-protected 'partially' PEGylated 2-arm peptidic core and unreacted fluorescein-PEG5 kDa in both curves.
Figure 10:
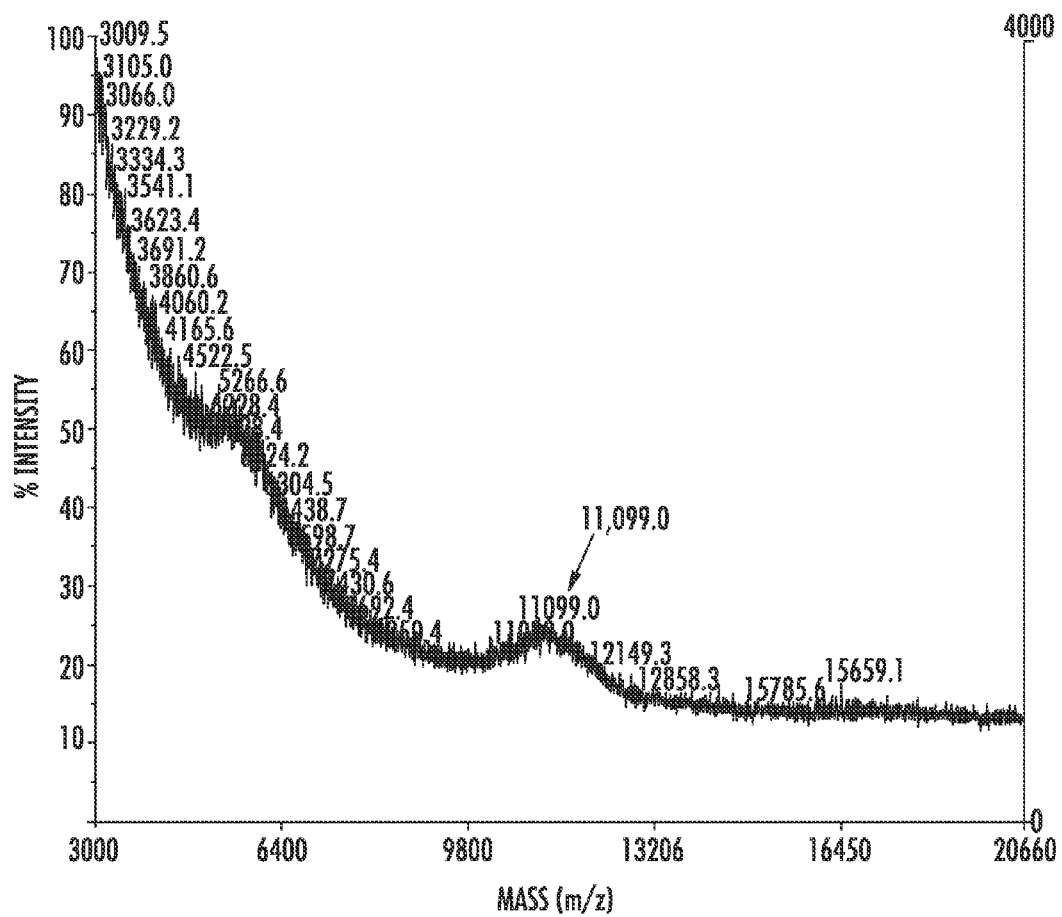
FIG. 10 is a MALDI-TOF (m/z) spectrum of purified labeled Cys-protected fully PEGylated 2-arm peptidic core. The peak showing molecular weight of 11,099.0 Da confirms attachments of two fluorescein-PEG5 kDa to the 2-arm peptidic core.
Figure 11A:
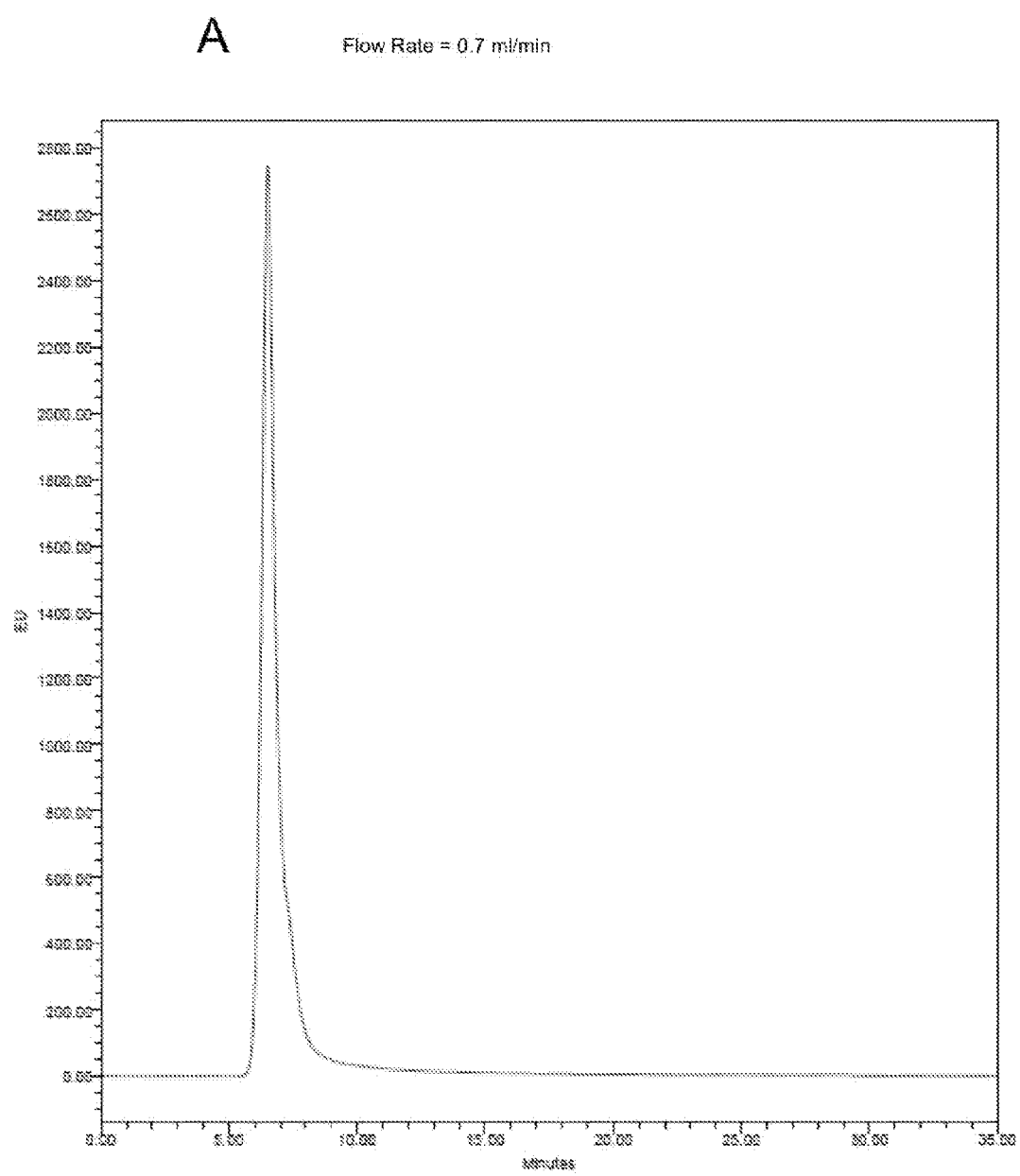
FIG. 11 is a HPLC chromatogram of purified Cys-protected PEGylated 2-arm peptidic core (A, C), crude homodimeric peptide-based PEG nanocarrrier (E) and crude homodimeric nanocarrier spiked with purified Cys-protected PEGylated 2-arm peptidic core (B, D, F). Different flow rates have been used to obtain better resolution. Spiking was performed to confirm the formation of the homodimeric nanocarrier and for better visualization.
Figure 11B:
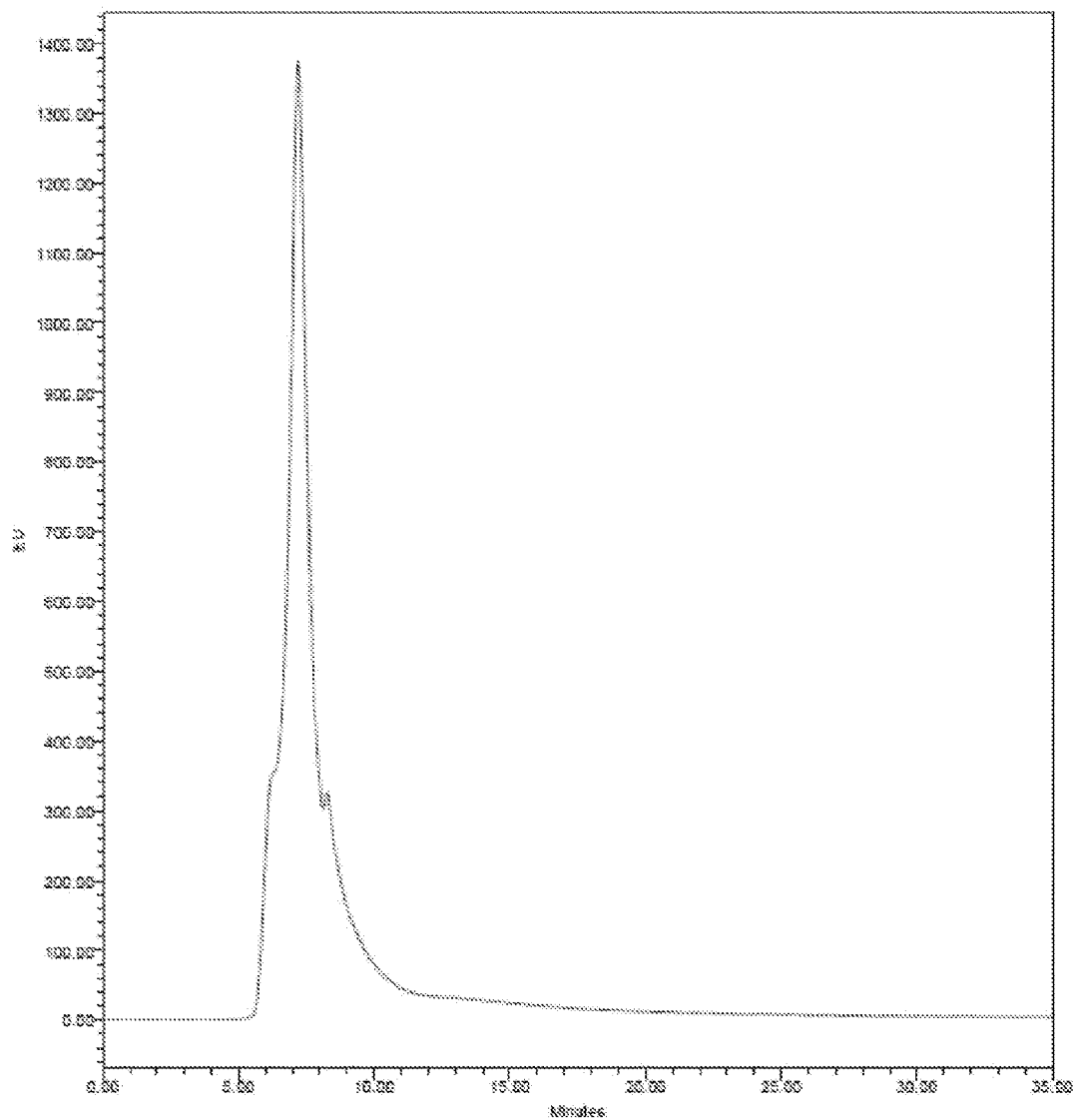
Figure 11C:
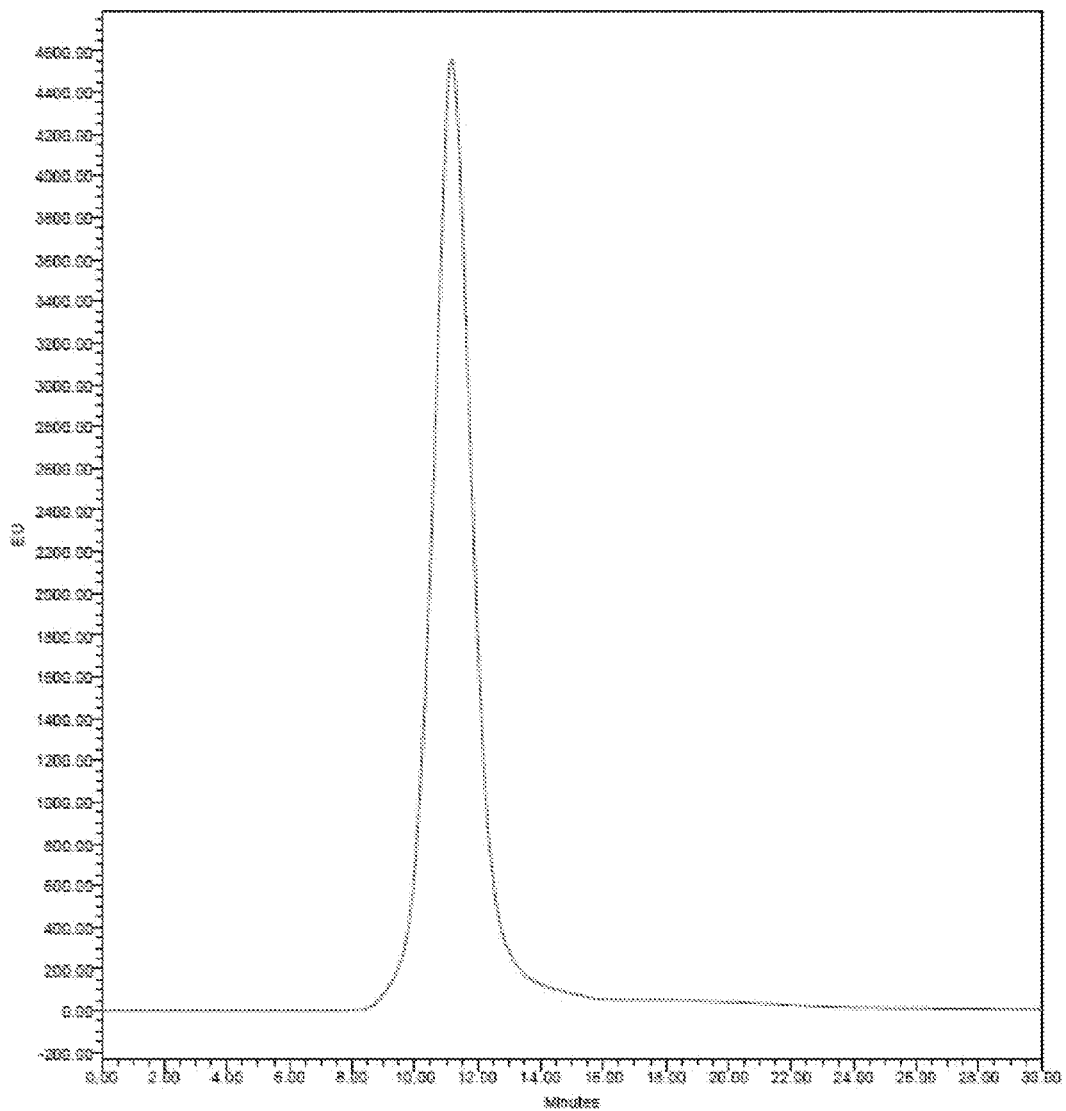
Figure 11D:
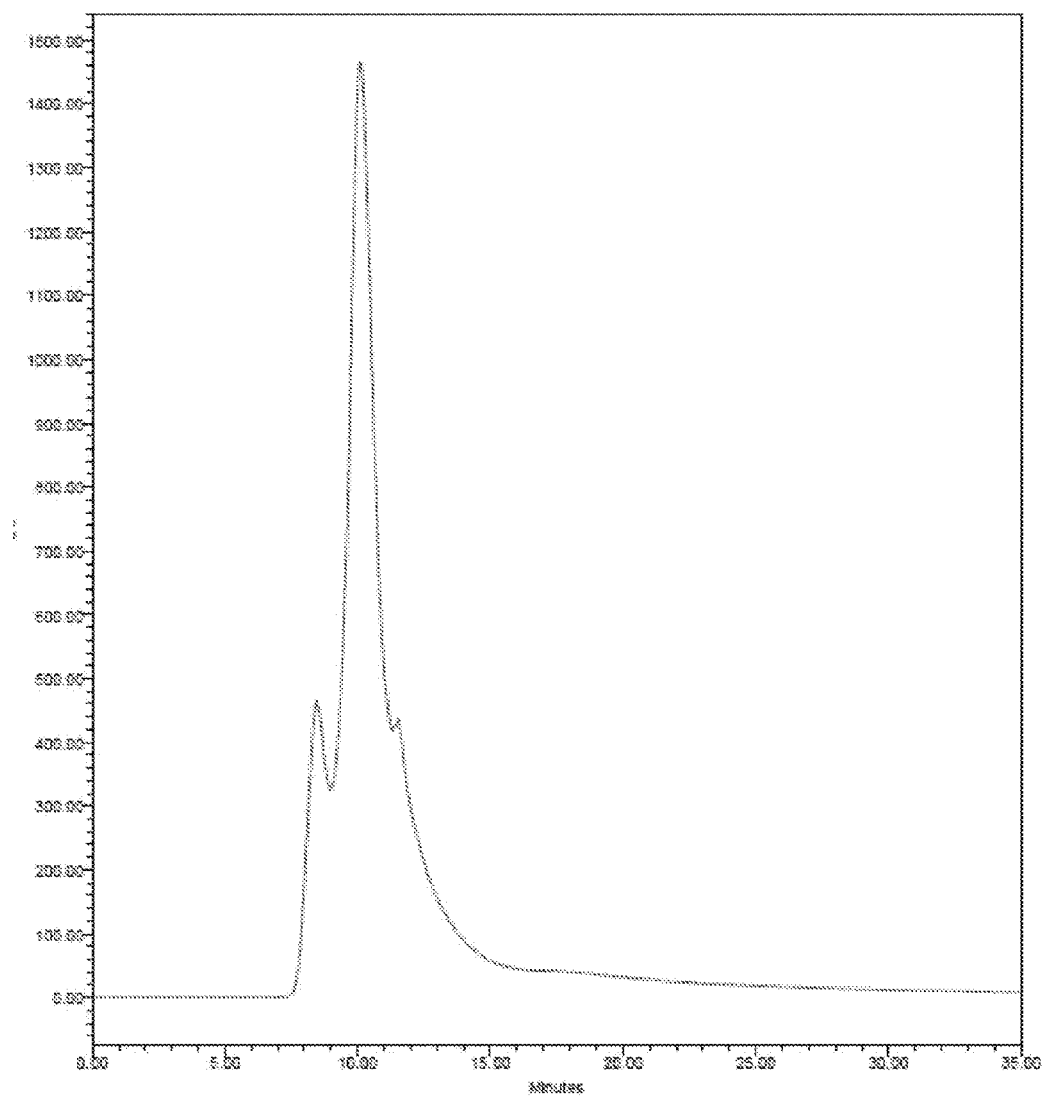
Figure 11E:
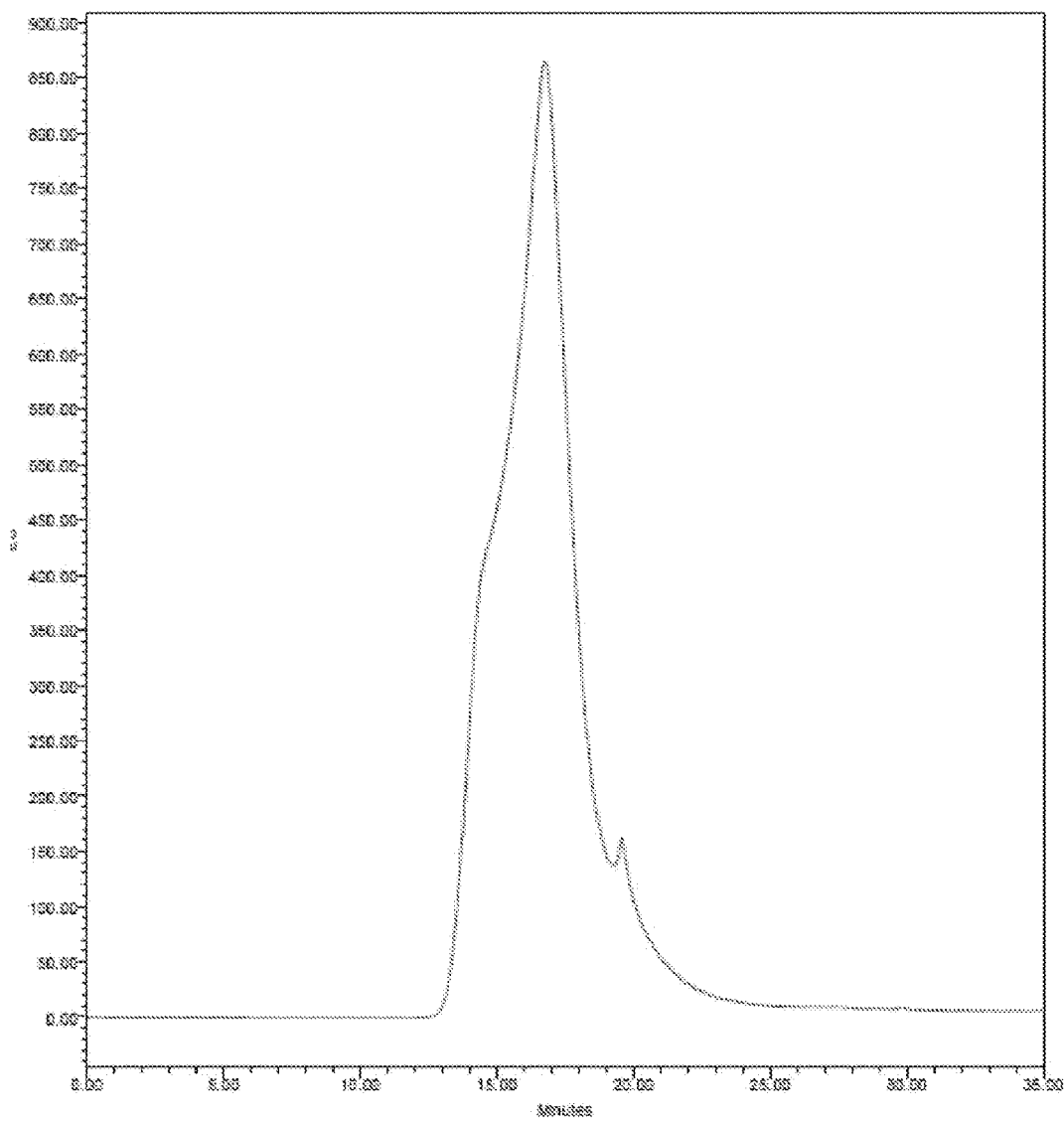
Figure 11F:
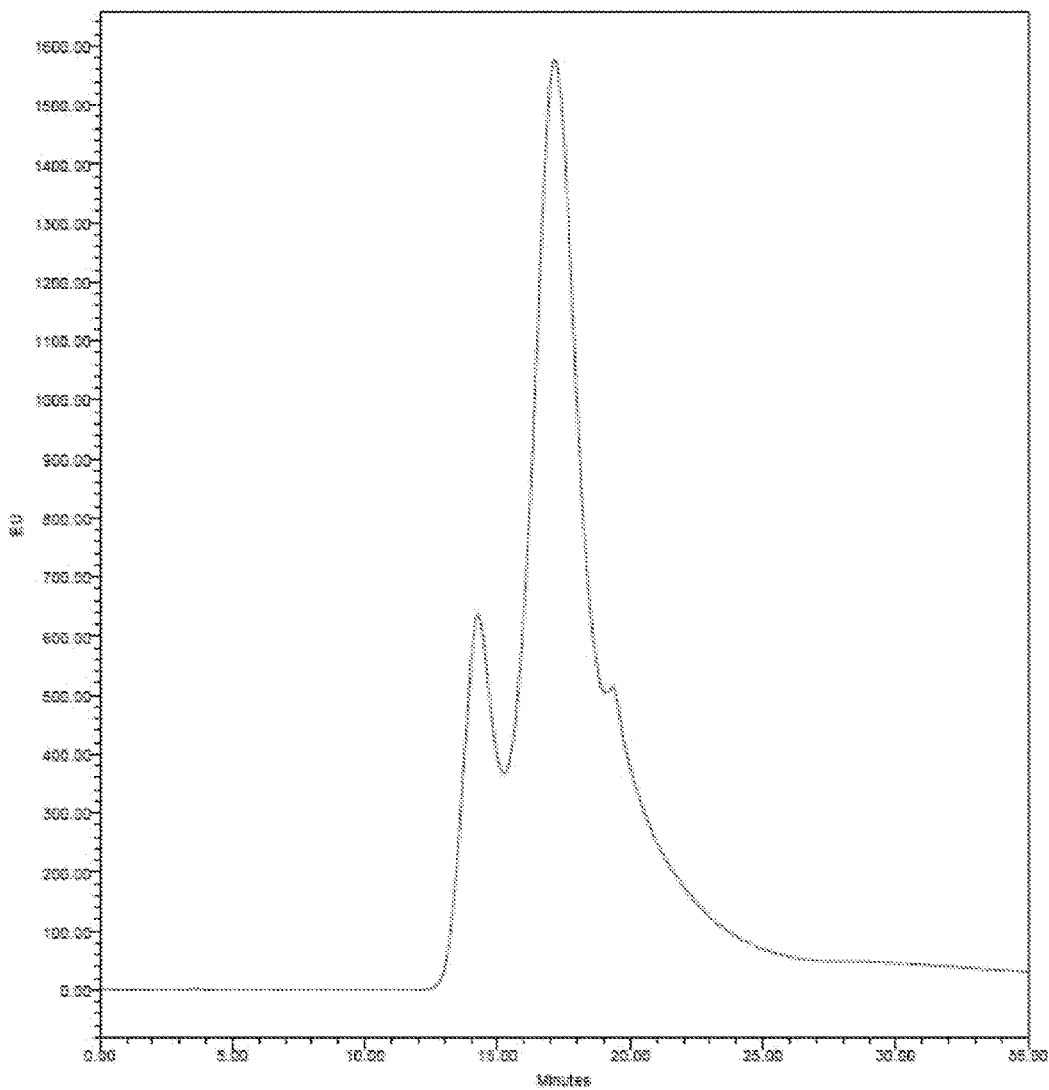

Fluorescein-labeled Cys-protected PEGylated 2-arm peptidic core: The PEGylation reaction of the Cys-protected peptidic core with 2 possible attachment sites (2-arm) at lysine was performed with 3 molar excess of fluorescein-PEG5 kDa-NHS dissolved in 30% or 70% (v:v) of DMSO in 100 mM PB pH 7.4±0.2 (FIG. 5). The addition of activated PEG was performed over a period of one hour using four equal aliquots. The reaction was kept at room temperature for 16 hours. Sephadex G-75 (medium) was soaked in PB pH 7.4±0.2 overnight and loaded onto a 50 cm Sephadex column. The PEGylated product was purified using gel permeation chromatography at a rate of approximately 0.8 ml/min. The fluorescence intensities of each fraction were detected using a microplate reader at $E_x$=485 nm and $E_m$=535 nm (FIG. 9). The first peak fractions for each chromatographic run were combined and concentrated using ultrafiltration (Amicon Ultra 30 kDa). The structure of the purified fluorescein-labeled PEGylated 2-arm peptidic core was confirmed using MALDI-TOF (FIG. 10).

Deprotection of fluorescein-labeled Cys-protected PEGylated 2-arm peptidic core: In order to remove thiopyridine from the Cys-protected PEGylated 2-arm peptidic core, it was dissolved in 20 molar equivalents of DTT in 100 mM PB at pH 8.0±0.2 and left at room temperature for 2 hours (FIG. 5). Unreacted DTT was removed using gel permeation chromatography on a Sephadex G-75 column in PB at pH 5.5±0.2. The effluent was concentrated and washed with PB pH 7.4±0.2 using a 10 kDa MWCO Microcon filter.

Fluorescein-labeled homodimeric peptide-based PEG nanocarrier: A fluorescein-PEG5 kDa-NHS standard curve was used to correlate fluorescence to molar concentration of the synthesized fluorescein-labeled Cys-protected PEGylated 2-arm peptidic core and its unprotected counterpart. The PEGylated peptidic cores dissolved in 100 mM PB pH 7.4±0.2 were mixed and reacted for 16 hours at room temperature. The volume was reduced using ultrafiltration (Microcon 10 kDa MWCO) and dimerization (FIG. 5) was confirmed using size exclusion HPLC (FIG. 11).

Texas Red-labeled Cys-protected 4-arm peptidic core: The Texas Red addition on the Cys-protected peptidic core with 4 possible attachment sites (4-arm) at lysine was performed with 3 molar excess of Texas Red-NHS dissolved in 30% DMSO in 100 mM PB pH 7.4±0.2 (FIG. 6). The reaction was performed overnight at room temperature. After the completion of labeling, a final concentration of 10 mM Tris buffer pH 7.0±0.2 was added in order to quench unreacted Texas Red.

Figure 12:
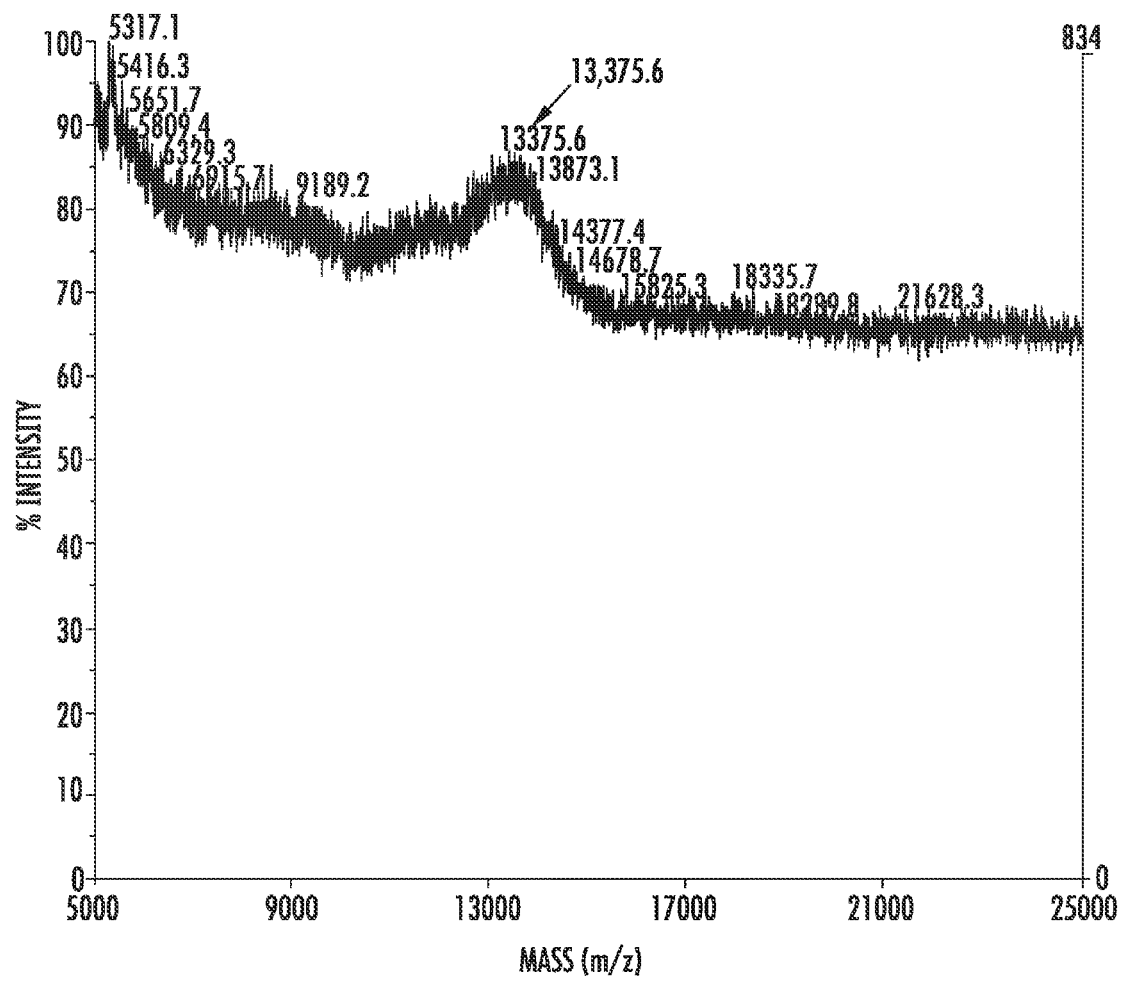
FIG. 12 is a MALDI-TOF (m/z) spectrum of purified heterodimeric peptide based PEG nanocarrier doubly labeled with fluorescein and Texas Red, showing a peak at molecular weight of 13,375.6 Da confirming the product.

Dual labeled heterodimeric peptide-based PEG nanocarrier: The dual labeled heterodimeric nanocarrier was prepared by reacting fluorescein-labeled Cys-unprotected PEGylated 2-arm peptidic core with equimolar amounts of Texas Red-labeled Cys-protected 4-arm peptidic core in 100 mM PB pH 7.4±0.2 (FIG. 6). The reaction was performed at room temperature overnight. Using a 10 kDa MWCO Microcon, the heterodimer was washed several times until the Texas Red fluorescence reading ($E_x$=530 nm, $E_m$=613 nm) in the filtrate was constant and insignificant. MALDI-TOF mass spectrometry confirmed the formation of heterodimer (FIG. 12).

Biodegradation of heterodimeric nanocarrier: The dual labeled heterodimeric nanocarrier was evaluated for its potential to biodegrade under simulated intracellular and extracellular/blood environments using 3 mM or 10 μM glutathione, respectively. To carry out the degradation studies, the nanocarrier was dissolved in 100 mM PB pH=7.4±0.2 containing of either 3 mM or 10 μM reduced GSH and incubated at 37° C. At each time points (0, 1, 3, 5, 7, 10 and 60 minutes; in case of 3 mM GSH) and (0, 15, 30, 60 and 90 minutes; in case of 10 μM GSH) solutions were aliquotted and treated with 1% TFA in order to stop the reaction. The TFA treated solution for each time-point was ultrafiltered (Microcon 10 kDa MWCO) for 20 minutes at 12,000×g to remove the released smaller sized Texas Red-labeled 4-arm peptidic core monomeric component. The retentate was washed 2 times with 1% TFA followed by ultrafiltration. The biodegradation was assessed using a microplate reader at $E_{max}$=530 nm, $E_m$=613 nm (for monitoring the reduction of Texas Red due to release of Texas Red-peptidic core monomer into the filtrate after degradation of the heterodimer) and at $E_x$=485 nm, $E_m$=535 nm (for monitoring the constant signal of free fluorescein-PEGylated peptidic core monomer in the retentate after degradation of the heterodimer) (FIGS. 10, 11). All experiments were performed in triplicate.

Since the oxidation (and loss) of GSH could confound the stability results in prolonged studies, especially at low concentrations such as 10 μM, a chromogenic assay using 2,2'-dithiodipyridine (TP-TP) was used to validate if the reduced GSH concentration remained constant for the duration of the biodegradation study. In this assay, the reduced form of GSH reacts with TP-TP and releases the chromogenic component 2-thiopyridine (2'-TP) that was monitored at 343 nm using a microplate reader. The concentration of reduced GSH employed in this study was determined from the standard curve obtained by reacting 2-50 μM reduced GSH in 100 mM PB pH=7.4±0.2 with a 10 molar excess of TP-TP (dissolved in DMSO). A linear relationship between the concentration of reduced GSH and 2'-TP was observed ($R^2$=0.993). Absorbance at 343 nm remained constant during the 2 hours of incubation at 37° C. suggesting that GSH was not oxidized during the biodegradation experiment and the concentration of reduced GSH remained constant (~10 μM).

It is widely believed that by treating only disease affected cells; drug dosages and side effects can be reduced, thus improving therapeutic outcomes. As such, drug targeting is an important goal in the treatment of AIDS or cancer since specific cell populations are involved in those diseases. To date, most targeting strategies have focused on controlling the initial distribution of delivery vehicles to the site of the disease. The most commonly used approach involves the selective delivery of drugs to specific cell types using a particulate carrier (e.g., liposomes or nanoparticles) or soluble nanocarriers (e.g., drug-polymer conjugates) with attached cell surface targeting ligands. The specificity of delivery is related to many factors including the type and number of targeting ligands required for optimal cellular uptake. Intracellular disposition and fate are highly dependent on the type of cell surface receptor and may require an additional strategy to promote endosomal escape. Previously, the inventors developed first generation nanocarriers using the chemo-attractant peptide, N-formyl-Met-Leu-Phe (fMLF), which were capable of actively targeting macrophages in vitro and in vivo. fMLF was selected as the first targeting ligand for the nanocarriers since the goal was to target macrophages, a phagocytic cell that plays a significant role in the persistence of HIV infection. The inventors also recently showed that intracellular distribution could be controlled by using a Tat peptide to facilitate endosomal escape. This is particularly important for drugs that are hydrophilic and act in the cytosol or must gain access to the nuclear compartment.

In this invention, the focus is shifted to the post-initial body distribution phase. In the current studies, second-generation multimeric peptide-backbone PEG nanocarriers (FIGS. 2, 5 and 6) were designed, synthesized, and characterized with the goal of building in specific body intracellular drug release and elimination properties. A biodegradable nanocarrier that is relatively stable in the blood circulation, while being selectively degraded inside target cells, was designed in order to exploit the natural extracellular-intracellular gradient of reducing conditions. The result is that the glutathione-sensitive disulfide bond between the monomeric peptidic units of the nanocarrier is cleaved releasing components with known body elimination pathways.

Example 1

PEGylation Reaction of Nanocarrier Monomer

In the current design, the free ε-amine groups of lysines on the 2-arm central peptidic core [acetylated-Lys-βAla-βAla-Lys-βAla-βAla-Cys(TP)-amidated] and the 4-arm central peptidic core [acetylated-Lys-βAla-βAla-Lys-βAla-βAla-Lys-βAla-βAla-Lys-βAla-βAla-Cys(TP)-amidated] are used for the attachment of fluorescein-PEG5 kDa and Texas Red, respectively, (FIGS. 5 and 6). Thus, it is necessary to quantify the amount of free amines present on the peptidic cores prior to PEGylation or labeling. The most common method used for quantification of peptides having primary amines is based on fluorescamine, a heterocyclic dione reagent that reacts with primary amines to form a fluorescent product. However, fluorescamine also reacts with water at lower rates and peptides/polypeptides tend to absorb moisture from the air. This side reaction often leads to inaccurate measurements. Therefore, a Kaiser chromogenic assay was selected over the conventional fluorescamine assay in order to quantify the peptides used in the current study. Since this assay is typically used to quantify primary amines of peptides during solid phase synthesis, it was modified and standardized for quantification of peptides in the liquid phase. The assay was successfully adapted and a typical standard curve (FIG. 7) demonstrated a strong correlation ($R^2$=0.993) between the amount of primary amines in the 2- and 4-arm peptidic cores and the released chromogenic product.

An inherent problem associated with PEGs is polydispersity. This is particularly true at higher molecular weights. A goal of the current study was to design a nanocarrier with low polydispersity and high yield. As size is a critical determinant of the biodistribution and body persistence of nanocarrriers, high polydispersity is expected to lead to high bioavailability variability and possibly to negative therapeutic outcomes. Lower molecular weight PEGs (~3-5 kDa) have polydispersity values as low as 1.01 whereas they can be as high as 1.2 for larger molecular weight PEGs (~20 kDa). Another complicating factor is the presence of the impurity diol, which ranges from 1-15% depending on the molecular weight of PEG. The diol content in low-mass PEGs (~1%) is much lower than that for higher molecular weight PEGs (~15%). High diol concentrations lead to unwanted aggregates or cross-linked products resulting in a low yield of the desired product. Therefore, it was hypothesized that attaching multiple low mass PEGs to the peptidic core would result in a higher yield of less polydisperse PEG nanocarriers as compared to attaching a single large PEG. Each PEG unit is attached in close proximity to each other on the peptide backbone resembling a branched or comb structure (FIGS. 2, 5 and 6). The PEGylated portion of the nanocarrier resembles a branched PEG similar to PEG2, a second generation PEG. Since branched PEGs have a relatively higher rate of hydration as compared to their linear counterparts, the viscosity radius of a protein that was PEGylated with four copies of a 5 kDa PEG was equivalent to PEGylation with a single 20 kDa PEG. This also appears to hold true for the pharmacokinetics of PEGylated proteins. For example, Knauf et al. demonstrated that the systemic clearance and elimination half-life of recombinant interleukin-2 that was PEGylated with multiple smaller PEGs or one larger PEG was essentially the same in rats. Taken together, these results suggest that the final topology and effective size of the nanocarrier is what determines biological functionality.

Achieving complete PEGylation of all of the ε-amine moieties on the peptidic core was challenging. As demonstrated by MALDI-TOF analysis, the initial PEGylation of a 6 lysine peptidic core where each lysine was separated by only one copy of β-alanine resulted in heterogeneous products containing 2-6 copies of PEG3.4 kDa (FIG. 8). It was hypothesized that due to the close proximity of lysine, the PEGylation reaction was hindered. This was addressed by designing a peptidic core consisting of 4 internal lysines (i.e., a 4-arm central peptidic core) with two β-alanine residues repeated after each lysine moiety in order to provide adequate spacing. This spacing was found to be favorable for entry and conjugation of a large diameter (5 kDa) hydrated activated PEG. However, the analytical Kaiser assay indicated that only 50% of the total ε-amines reacted. This represented a significant improvement over the 30% PEGylation observed with the single β-alanine spacer in the peptidic core. However, total PEG content was still low considering that the target molecular size of the nanocarrier should ideally be between 20 kDa and 40 kDa. This issue was addressed by designing a peptidic core with 2 lysine PEG attachment sites and increasing PEG content by dimerizing the purified 2-arm PEGylated product (FIG. 5). The purification of the PEGylated product using a G-75 Sephadex column is shown in FIG. 9. When the fluorescein-PEG 5 kDa-NHS polymer was loaded by itself onto the column a single peak was obtained. The higher mobility peak corresponds to the 'fully' PEGylated product and the lower mobility peak represents a combination of excess unreacted fluorescein-PEG5 kDa-NHS and 'partially' PEGylated peptidic core (FIG. 9). The mass of the higher mobility PEGylated product was determined by MALDI-TOF (FIG. 10). The expected molecular weight very closely matched the theoretical value confirming the formation of the PEGylated product (FIG. 5). Each ethylene glycol subunit is associated with two or three water molecules that impart a high hydrodynamic volume to the PEG resulting in a 5-10 fold increase in effective size. Higher DMSO concentrations (70%) resulted in a high PEGylated product yield (69%) whereas the low DMSO conditions resulted in a much lower yield of 32%. It appears that high aqueous conditions (i.e., low DMSO concentrations) lead to higher hydrodynamic volume and high steric hindrance resulting in dramatically reduced PEGylation product yield. Conversely, increasing the DMSO concentration resulted in an environment where PEG is not fully hydrated, steric hindrance is reduced and a higher PEGylated product yield is obtained. Therefore, higher concentrations of DMSO along with 2 copies of β-alanine spacer are crucial for successful PEGylation of peptidic core.

Example 2

Homodimerization of Peptide-Based PEG Nanocarrier

The presence of cysteine in the peptidic core enables the production of a dimeric second-generation nanocarrier. By using the multimer approach, the body elimination pathway can be precisely programmed into the nanocarrier design. This is achieved by controlling the degree of branching and the size of the monomers. The current design did not specifically include the cleavage of the monomer to its peptide and PEG components since the peptide did not contribute significantly to the overall size and the monomer size is below the renal filtration threshold. The homodimeric nanocarrier consisted of two monomers of a PEGylated 2-arm peptidic core monomer carrying 2 copies of 5 kDa PEG-fluorescein) linked via a disulfide bond (FIG. 5). This design resulted in a nanocarrier with a MW of 21,950 Da. By reacting an equimolar amount of purified thiopyridine protected PEGylated 2-arm peptidic core with its unprotected counterpart, homodimerization was achieved (FIG. 5). The purified Cys-protected PEGylated 2-arm peptidic core generated single peaks at retention times of ~7 and ~11 minutes at flow rates of 0.7 and 0.5 ml/min, respectively, using size exclusion-HPLC (FIG. 11; Panels A and C). At flow rate of 0.3 ml/min, the crude homodimerization product exhibited a visible shoulder with slower mobility (FIG. 11, Panel E). In order to further resolve the product, the crude product was spiked with purified Cys-protected PEGylated 2-arm peptidic core (FIG. 11; Panel F) at the same flow rate. This addition proved to be crucial for visualization of the dimerized product. At flow rates of 0.5 and 0.7 ml/min the homodimerized product was observed as a distinct shoulder with slower mobility (FIG. 11; Panels B and D) when spiked with free PEGylated 2-arm peptidic core. The flow rate of 0.3 ml/min gave the best resolution with minimal absorptive loss.

Example 3

Figure 13:
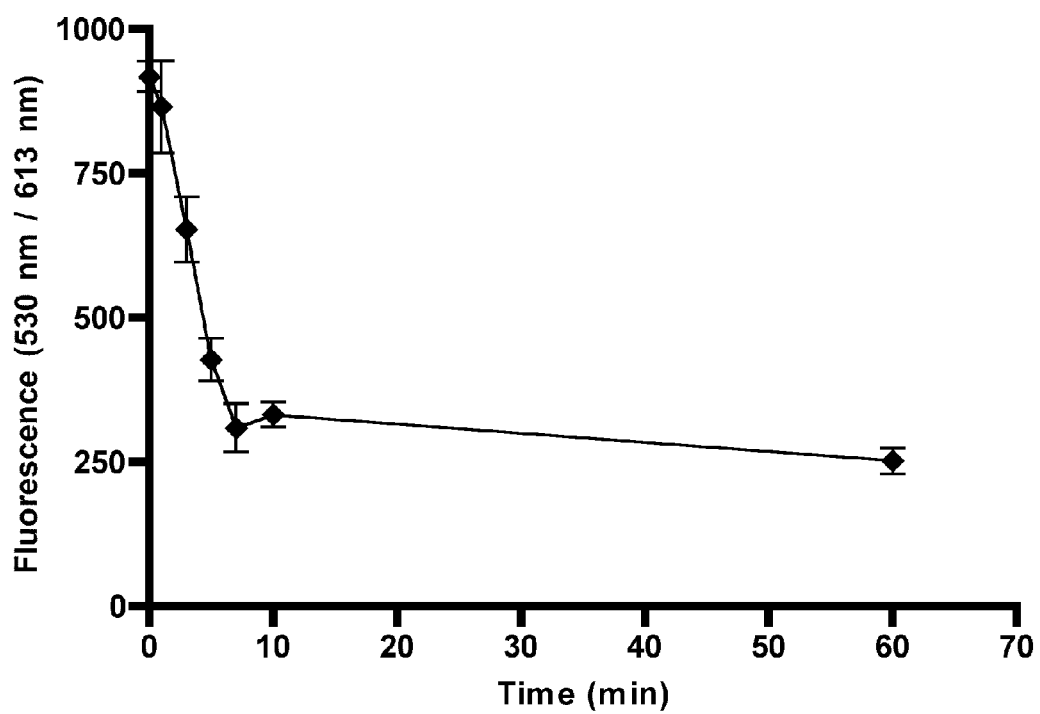
FIG. 13 is a time course release of the dual labeled biodegradable nanocarrier in 3 mM GSH at 37° C.: The heterodimeric nanocarrier was dissolved in 100 mM PB pH 7.4±0.2 in presence of 3 mM reduced GSH. At each time point (0, 1, 3, 5, 7, 10 and 60 minutes), 1% TFA was added to the sample to stop the reduction reaction. The zero time point is identical to other sample with the exception that it did not contain any GSH. All experiments were performed in triplicate.
Figure 14:
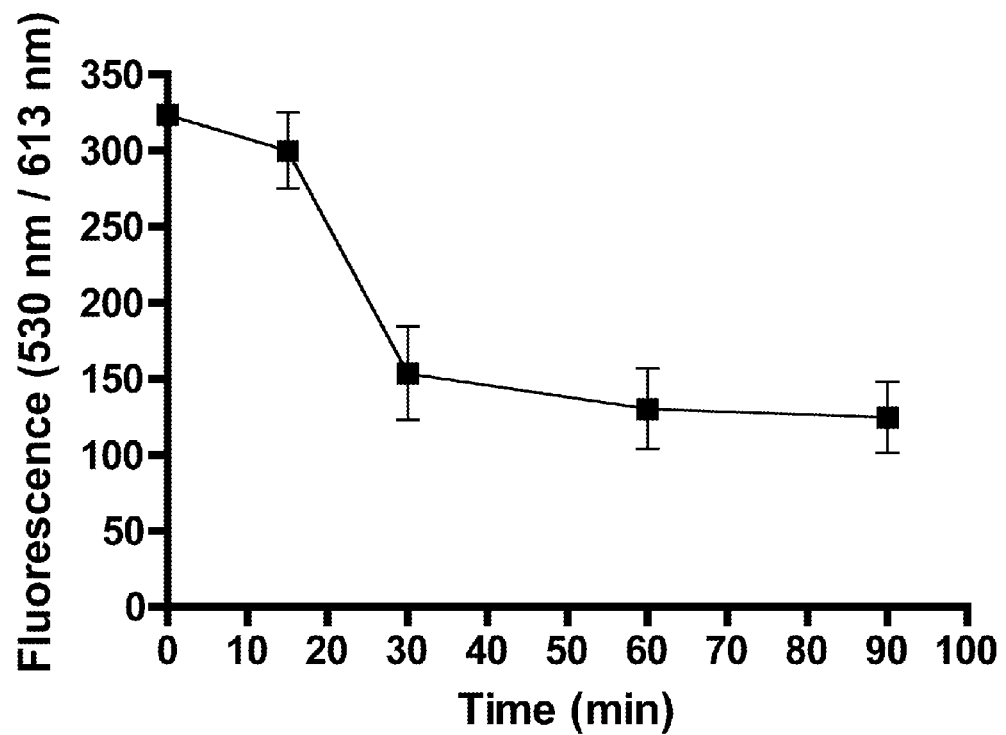
FIG. 14 is a time course release of the dual labeled biodegradable nanocarrier in 10 μM GSH at 37° C.: The heterodimeric nanocarrier was dissolved in 100 mM PB pH 7.4±0.2 in presence of 10 μM reduced GSH. At each time point (0, 15, 30, 60 and 90 minutes), 1% TFA was added to the sample to stop the reduction reaction by GSH. The zero time point is identical to other sample with the exception that it did not contain any GSH. All experiments were performed in triplicate.

Heterodimeric Peptide-Based PEG Nanocarrier and its Biodegradation Characteristics A dual labeled heterodimeric nanocarrier consisting of a PEGylated 2-arm peptidic core monomer carrying two copies of Fluorescein-PEG5 kDa and a non-PEGylated 4-arm peptidic core monomer carrying four copies of Texas Red linked via a disulfide bond was prepared for the purposes of assessing its potential for biodegradation (FIG. 6). The purified heterodimeric nanocarrier was subjected to MALDI-TOF mass spectrometry (FIG. 12). The obtained mass exhibited an increase to 13,375 Da consistent with the expected increase in molecular weight confirming the presence of the product. The biodegradation of the nanocarrier was investigated in environments that mimic the reducing concentration in blood (10 µM GSH) or inside cells (3 mM GSH). The reduction of the disulfide linkage and subsequent release of the nanocarrier monomers was monitored at each time-point by stopping the reaction using an acidifying solution. The small 4-arm peptidic core monomer carrying Texas Red passed through a 10 kDa MWCO filter while the free fluorescein-PEGylated 2-arm peptidic core is retained on the filter. Thus, simulated biodegradation was monitored by the reduction in the Texas Red fluorescence signal. The Texas Red fluorescence signal in the retentate is attributed to the intact heterodimeric nanocarrier. Biodegradation in the presence of 3 mM GSH at 37° C. resulted in complete release of the Texas Red labeled 4-arm monomer from the intact heterodimeric nanocarrier in 7 minutes (FIG. 13). When the solution containing the heterodimer was modified to a final concentration of 1% TFA prior to the addition of GSH, release was not observed and the values were nearly identical to the zero time-point even after 2 hours of incubation at 37° C. This demonstrates that acidifying the solution stopped the reaction thus allowing for proper temporal quantification of biodegradation. In addition, the fluorescein tag remained attached to terminal end of PEG during the study as evidenced by a lack of signal at $E_x$=485 nm; $E_m$=535 nm from the filtrate. Therefore, at conditions that mimic the reducing environment inside the cell, the heterodimeric nanocarrier showed complete degradation to its monomeric components. Upon incubation of the doubly labeled nanocarrier in 10 µM GSH, biodegradation to its component monomers was complete after 60 minutes (FIG. 14). Prolonged incubation or addition of excess GSH (3 mM for one hour) did not further reduce the fluorescence reading. Since the oxidation and loss of GSH during the time course of the study was not observed, the stabilization method was considered valid. Although the nanocarrier was stable for ~1 hour in a reducing environment similar to the blood, the target blood stability is probably in the range of 24 hours or so in order to provide adequate exposure of the nanocarrier to affected cells. Our group and others have shown that the rate of biodegradation of the disulfide linkage can be manipulated by altering steric hindrance. For example, a disulfide bond prepared from a sterically hindered cysteamine analogue linker, 1-amino-2-methyl-2-propanethiol, showed about 100-times slower degradation rate than that of the corresponding less hindered cysteamine linker ($t_{1/2}$ of GSH-dependent disulfide degradation=3 min). The introduction of sterically hindered methyl groups to the peptidic core adjacent to the cysteine residue may result in a longer persistence for intact nanocarrier. Since the disulfide cleavage rate is proportional to glutathione concentration, the rate of biodegradation can be readily controlled by selection of such sterically hindered cysteines in the peptidic backbone of the nanocarrier prior to disulfide bond formation. In addition to using disulfide bonds, more stable carbamate or ester linkages can also be used to prolong the biodegradation rate.

In the current studies, a second-generation peptidic core monomer was identified that allowed for optimal attachment of multiple PEGs in stoichiometric amounts with low polydispersity. High product yields were obtained by selecting the optimal spacing requirements in the peptide core and by using high concentrations of DMSO to reduce the hydrodynamic volume of solvated PEG. Homodimeric and heterodimeric biodegradable nanocarriers were synthesized and characterized from PEGylated and non-PEGylated peptide cores. Selective intracellular biodegradation was observed in vitro. The modular synthesis of these nanocarriers has the advantage of minimizing polydispersity, a challenge that is always present with polymeric nanocarriers. The design is sufficiently flexible so that the component peptidic monomers could be used to link PEGs, imaging agents, drugs, targeting ligands or other peptidic cores. Two important design components, the biodegradable bonds between monomeric peptidic core units and using PEGs of the appropriate size in order to promote renal or hepatic elimination, allows for the pre-programming of body elimination properties into the nanocarrier.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

The invention claimed is:

1. A biodegradable multimeric nanocarrier for in vivo delivery of a bioactive agent, comprising at least two peptide monomers reversibly or irreversibly linked with one or more of said bioactive agents, wherein
each of said peptide monomers having Formula II:

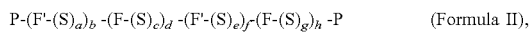

$$P\text{-}(F'\text{-}(S)_a)_b\text{-}(F\text{-}(S)_c)_d\text{-}(F'\text{-}(S)_e)_f\text{-}(F\text{-}(S)_g)_h\text{-}P \quad \text{(Formula II)},$$

wherein independently for each of said peptide monomers:
P is an optional protection group of at least one of the C- and N- terminal of the peptide monomer;
F' is a functional amino acid and is cysteine;
F is a functional amino acid capable of linking to a bioactive agent, wherein
F is selected from the group consisting of lysine, arginine, cysteine, glutamic acid, aspartic acid, diaminobutyric acid, histidine, threonine, serine, and tyrosine, and wherein at least one F is linked directly or via a PEG linker to at least one imaging agent, targeting ligand or a drug;
S is a spacer amino acid;
a, c, d, e and g are each an integer between 1 and 10, inclusive;
b and d are each an integer between 1 and 9 inclusive, f and h are each an integer between 0 and 9, inclusive, provided that the sum of b, d, f and h is between 2 and 10 inclusive; and
wherein a first peptide monomer according to Formula II is covalently linked to a second peptide monomer according to Formula II by a biodegradable difunctional moiety consisting of a disulfide bond between their respective F' amino acids.

2. The biodegradable multimeric nanocarrier according to claim 1, wherein at least one of the F functional amino acids is a L- or D-amino acid.

3. The biodegradable multimeric nanocarrier according to claim 1, wherein the spacer consists of β-alanine, alanine, gamma-amino butyric acid (GABA), glycine or any combination thereof.

4. The biodegradable multimeric nanocarrier according to claim 1, wherein said peptide monomers are independently selected from the group consisting of SEQ ID NOS: 1-8.

5. The biodegradable multimeric nanocarrier according to claim 1, wherein said peptide monomers have identical amino acid sequences.

6. The biodegradable multimeric nanocarrier according to claim 1, wherein said peptide monomers have different amino acid sequences.

7. The biodegradable multimeric nanocarrier according to claim 1, comprising at least three of said peptide monomers.

8. The biodegradable multimeric nanocarrier according to claim 1, wherein said at least one of said F functional amino acids is covalently bound to the bioactive agent directly or via the PEG linker by a reversible linkage.

9. The biodegradable multimeric nanocarrier according to claim 1, wherein said at least one of said F functional amino acids is covalently bound to the bioactive agent directly or via the PEG linker by an irreversible linkage.

10. The biodegradable multimeric nanocarrier according to claim 1, wherein said bioactive agent is a drug selected from the group consisting of anti-inflammatory drugs, sancycline and sancycline analogs, olvanil and olvanil analogs, retro-olvanil and retro-olvanil analogs, olvanil carbamate, budesonide and budesonide analogs, ethylprenisolone 30, methylprenisolone and methylprenisolone analogs, dexamethasone and dexamethasone analogs, anticancer drugs, anti-HIV drugs and monoclonal antibodies.

11. The biodegradable multimeric nanocarrier according to claim 1, wherein said bioactive agent is an imaging agent selected from the group consisting of coloring dyes and visible/near infrared fluorescence dyes.

12. The biodegradable multimeric nanocarrier according to claim 1, wherein at least one of said is peptide monomers comprises a targeting ligand selected from the group consisting of vitamins, carbohydrates for which a transporter exists, chemotactic peptides, enzymes, antibodies or antibody fragments with specific affinity for lymphocyte subpopulations, neurons and other cell type antigens and epitopes, hormones, adhesion molecules, lipids and oligonucleotides.

13. The biodegradable multimeric nanocarrier according to claim 1, wherein at least about 50 percent of said F functional amino acids are bound to the bioactive agent directly or via the PEG linker.

14. The biodegradable multimeric nanocarrier according to claim 1, wherein said PEG linker is a straight or branched PEG having 2 to 8 arms.

15. The biodegradable multimeric nanocarrier according to claim 1, wherein said PEG linker is a straight PEG linker having length of 1000 to 10000 Da, or wherein said PEG is a branched PEG having 2 to 8 arms, each of said arms having length of 1000 to 10000 Da.

16. A method of treating a mammal diagnosed with a disease, comprising administering to said mammal an effective amount of the nanocarrier according to claim 1, wherein the nanocarrier comprises a bioactive agent effective to treat the disease.

17. A method of diagnosing a disease in a mammal comprising administering to said mammal an effective amount of the nanocarrier according to claim 1, wherein the nanocarrier comprises an agent for diagnosing said disease.

18. The method of claim 16 or 17, wherein the mammal is a human.

19. The nanocarrier according to claim 1, wherein said first peptide monomer is further covalently linked to a third peptide monomer according to Formula II by a biodegradable difunctional moiety consisting of a disulfide bond between their respective F' amino acids.

* * * * *

UNITED STATES PATENT AND TRADEMARK OFFICE
CERTIFICATE OF CORRECTION

PATENT NO. : 9,421,272 B2
APPLICATION NO. : 13/255635
DATED : August 23, 2016
INVENTOR(S) : Patrick J. Sinko et al.

Page 1 of 1

It is certified that error appears in the above-identified patent and that said Letters Patent is hereby corrected as shown below:

In the Specification

Column 1 Lines 13-16 Delete the Statement Regarding Governmental Support and replace with:
"This invention was made with government support under grant number AI051214 awarded by the National Institutes of Health. The government has certain rights in the invention."

Signed and Sealed this
Third Day of October, 2023

Katherine Kelly Vidal
*Director of the United States Patent and Trademark Office*